(12) United States Patent
Sliwa et al.

(10) Patent No.: US 10,980,598 B2
(45) Date of Patent: Apr. 20, 2021

(54) MULTI-ELECTRODE ABLATOR TIP HAVING DUAL-MODE, OMNI-DIRECTIONAL FEEDBACK CAPABILITIES

(71) Applicant: St. Jude Medical, Cardiology Division, Inc., St. Paul, MN (US)

(72) Inventors: John W. Sliwa, San Jose, CA (US); Zhenyi Ma, Santa Clara, CA (US); Stephen A. Morse, Menlo Park, CA (US); John A. Hauck, Shoreview, MN (US); Don Curtis Deno, Andover, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 265 days.

(21) Appl. No.: 15/355,201

(22) Filed: Nov. 18, 2016

(65) Prior Publication Data

US 2017/0143414 A1  May 25, 2017

Related U.S. Application Data

(60) Provisional application No. 62/258,281, filed on Nov. 20, 2015.

(51) Int. Cl.
*A61B 18/14* (2006.01)
*A61B 18/00* (2006.01)

(52) U.S. Cl.
CPC ...... *A61B 18/1492* (2013.01); *A61B 2018/00083* (2013.01); *A61B 2018/00351* (2013.01);
(Continued)

(58) Field of Classification Search
CPC ........... A61B 2018/00083; A61B 2018/00351; A61B 2018/0057; A61B 2018/00797;
(Continued)

(56) References Cited

U.S. PATENT DOCUMENTS 5,462,545 A * 10/1995 Wang ................. A61B 18/1492
600/373
6,064,905 A * 5/2000 Webster, Jr. ......... A61B 5/0422
600/374
(Continued)

FOREIGN PATENT DOCUMENTS

EP    1 343 427 A1    9/2003
EP    2944282 A1    11/2014
(Continued)

OTHER PUBLICATIONS

Eitel, et al., Circumferential Pulmonary Vein Isolation and Linear Left Atrial Ablation as Single Catheter Technique to Achieve Bidirectional Conduction Block: the 'Pace-and-Ablate' Approach. Heart Rhythm Society 2010; 7: 157-164.

*Primary Examiner* — Michael F Peffley
(74) *Attorney, Agent, or Firm* — Dykema Gossett PLLC

(57) ABSTRACT

Electrode assemblies include segmented electrodes disposed on a catheter. The segmented electrodes can be constructed at the tip of the catheter. Tip electrodes can be constructed from an electrically insulative substrate comprising an inner lumen, an external tip surface, and a plurality of channels extending from the inner lumen to the external tip surface, a plurality of segmented electrodes, and a plurality of spot electrodes. Each of the plurality of segmented electrodes and each of the plurality of spot electrodes can be laterally separated from each other by an electrically non-conductive substrate portion and each of the spot electrodes and each of the segmented electrodes can be electrically coupled to at least one wire or conductor trace.

25 Claims, 12 Drawing Sheets

(52) U.S. Cl.
CPC ............ *A61B 2018/00577* (2013.01); *A61B 2018/00797* (2013.01); *A61B 2018/00839* (2013.01); *A61B 2018/00869* (2013.01); *A61B 2018/00875* (2013.01); *A61B 2018/00892* (2013.01); *A61B 2018/1417* (2013.01); *A61B 2018/1467* (2013.01); *A61B 2018/1497* (2013.01); *A61B 2218/002* (2013.01)

(58) Field of Classification Search
CPC .. A61B 2018/00939; A61B 208/00869; A61B 2018/00875; A61B 2018/00892; A61B 2018/1417; A61B 2018/1467; A61B 2018/1497; A61B 2218/002
See application file for complete search history.

(56) References Cited

U.S. PATENT DOCUMENTS

| | | | |
|---|---|---|---|
| 6,142,933 A | 11/2000 | Whayne et al. | |
| 6,241,724 B1* | 6/2001 | Fleischman | A61B 18/1492 600/374 |
| 7,263,397 B2 | 8/2007 | Hauck et al. | |
| 7,311,708 B2* | 12/2007 | McClurken | A61B 18/1492 606/50 |
| 7,885,707 B2 | 2/2011 | Hauck | |
| 8,414,579 B2* | 4/2013 | Kim | A61B 18/18 606/46 |
| 2004/0092806 A1* | 5/2004 | Sagon | A61B 5/0422 600/374 |
| 2008/0243214 A1* | 10/2008 | Koblish | A61B 5/0422 600/374 |
| 2009/0281541 A1 | 11/2009 | Ibrahim et al. | |
| 2010/0204691 A1 | 8/2010 | Bencini | |
| 2010/0331658 A1 | 12/2010 | Kim et al. | |
| 2012/0143177 A1 | 6/2012 | Avitall | |
| 2013/0158548 A1 | 6/2013 | Govari et al. | |
| 2013/0190747 A1 | 7/2013 | Koblish et al. | |
| 2013/0197507 A1 | 8/2013 | Kim et al. | |
| 2014/0052118 A1 | 2/2014 | Laske et al. | |
| 2014/0081111 A1 | 3/2014 | Tun et al. | |
| 2014/0081112 A1 | 3/2014 | Kim et al. | |
| 2014/0171821 A1 | 6/2014 | Govari et al. | |
| 2014/0243816 A1 | 8/2014 | Jimenez | |
| 2015/0133914 A1* | 5/2015 | Koblish | A61B 5/0422 606/34 |

FOREIGN PATENT DOCUMENTS

| | | |
|---|---|---|
| EP | 3040043 B1 | 1/2018 |
| WO | 95/10978 A1 | 4/1995 |
| WO | 9725917 A1 | 7/1997 |
| WO | 9858681 A2 | 12/1998 |
| WO | 02056783 A1 | 7/2002 |
| WO | 2014113612 A1 | 7/2014 |
| WO | 2014182822 A1 | 11/2014 |
| WO | 2015065966 A3 | 5/2015 |
| WO | 2015130824 A1 | 9/2015 |
| WO | 2015130829 A1 | 9/2015 |

* cited by examiner

US 10,980,598 B2

MULTI-ELECTRODE ABLATOR TIP HAVING DUAL-MODE, OMNI-DIRECTIONAL FEEDBACK CAPABILITIES

BACKGROUND

Field

The instant disclosure relates to ablation tips that have feedback capability. In one embodiment, the instant disclosure relates to ablation tips that provide dual-mode, omni-directional feedback so that lesion, mapping and/or force assessments can be made regardless of the orientation of the tip.

Background Art

Electrophysiology catheters are used in a variety of diagnostic and/or therapeutic medical procedures to diagnose and/or correct conditions such as atrial arrhythmias, including for example, ectopic atrial tachycardia, atrial fibrillation, and atrial flutter. Arrhythmias can create a variety of conditions including irregular heart rates, loss of synchronous atrioventricular contractions and stasis of blood flow in a chamber of a heart which can lead to a variety of symptomatic and asymptomatic ailments and even death.

A medical procedure in which an electrophysiology catheter is used includes a first diagnostic catheter deployed through a patient's vasculature to a patient's heart or a chamber or vein thereof. An electrophysiology catheter that carries one or more electrodes can be used for cardiac mapping or diagnosis, ablation and/or other therapy delivery modes, or both. Once at the intended site, treatment can include, for example, radio frequency (RF) ablation, cryoablation, laser ablation, chemical ablation, high-intensity focused ultrasound-based ablation, electroporation ablation or microwave ablation. An electrophysiology catheter imparts ablative energy to cardiac tissue to create one or more lesions in the cardiac tissue and oftentimes, a contiguous, and transmural lesion. This lesion disrupts undesirable cardiac activation pathways and thereby limits, corrals, or prevents errant conduction signals that can form or sustain arrhythmias.

BRIEF SUMMARY

The instant disclosure, in at least one embodiment, relates to a tip electrode of a catheter comprising an electrically-insulative substrate.

In one embodiment, tip electrode can comprise an electrically insulative substrate comprising an inner lumen, an external tip surface, and a plurality of channels extending from the inner lumen to the external tip surface, a plurality of segmented electrodes, and a plurality of spot electrodes. Each of the plurality of segmented electrodes and each of the plurality of spot electrodes can be laterally separated from each other by an electrically non-conductive substrate portion and each of the spot electrodes and each of the segmented electrodes can be electrically coupled to at least one wire or conductor trace.

In another embodiment of the disclosure, a system for ablating tissue can comprise a tip electrode comprising an electrically insulative substrate comprising an inner lumen, an external tip surface, and a plurality of channels extending from the inner lumen to the external tip surface, a plurality of segmented electrodes, and a plurality of spot electrodes. Each of the plurality of segmented electrodes and each of the plurality of spot electrodes can be laterally separated from each other by an electrically non-conductive substrate portion and each of the spot electrodes and each of the segmented electrodes can be electrically coupled to at least one wire or conductor. The system can further comprise an electronic control unit configured to control the plurality of spot electrodes and the plurality of segmented electrodes to bipolar pace cardiac tissue.

In yet another embodiment of the disclosure, a system for determining a tissue characteristic can comprise an electronic control unit configured to measure a pre-lesion impedance at a known temperature of a target site, measure an impedance at a known temperature of the target site after ablation has occurred, and utilize a model of lesion impedance behavior to determine a state of the target site.

In yet another embodiment of the disclosure, a system for determining a tissue characteristic can comprise an electronic unit configured to measure a heat flow ability of a target site before ablation has occurred, measure a heat flow ability of the target site after ablation has occurred, and use a thermal model of the target site to deduce at-least a depthwise temperature profile of the target site based on the before and after heat flow ability. The heat flow ability can be measured by changing a rate of heat accumulation in the target site and observing the corresponding change in a tissue surface temperature.

In yet another embodiment of the disclosure, a system for determining a tissue characteristic can comprise an electronic control unit configured to measure a pre-lesion impedance at a known temperature of a target site, measure an impedance at a known temperature of the target site after some ablation has occurred, utilize a model of lesion impedance behavior to determine a state of the target site, measure a heat flow ability of the target site before some ablation has occurred, measure a heat flow ability of the target site after some ablation has occurred, utilize a thermal model of the target site to obtain at-least a depthwise temperature profile of the target site based on the before and after heat flow, and employ both results via a weighting of the two results to determine a weighted lesion state.

DETAILED DESCRIPTION

Figure 1:
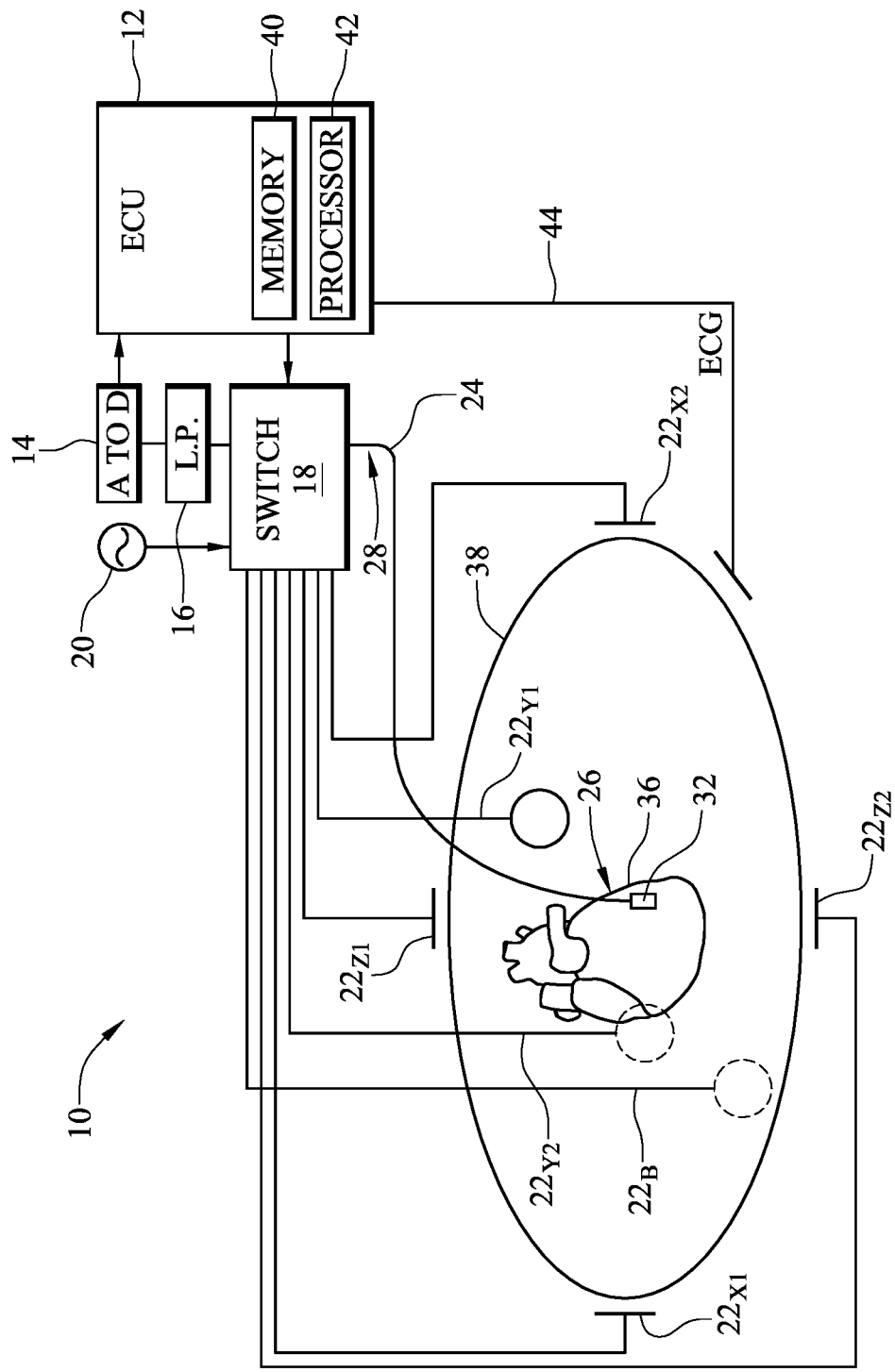
FIG. 1 is a diagrammatic depiction of an exemplary intracardiac mapping and navigation system for use with various medical devices that are capable of utilizing an electrode assembly with dual-mode, omni-directional feedback capabilities of the present disclosure.
Figure 2A:
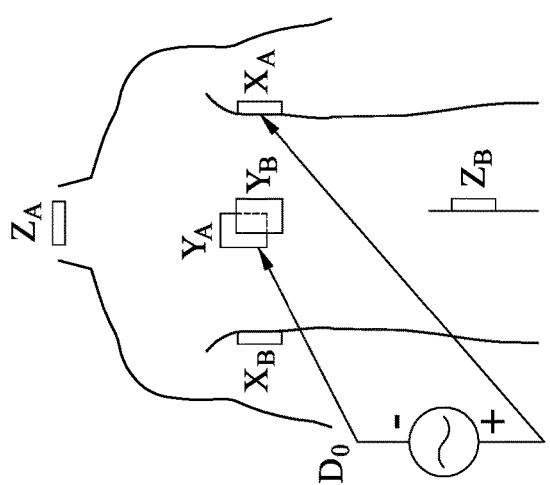
FIGS. 2A-2D are schematic diagrams of exemplary bipole pairs of driven body patch electrodes suitable for use with the intracardiac mapping and navigation system of FIG. 1.
Figure 2B:
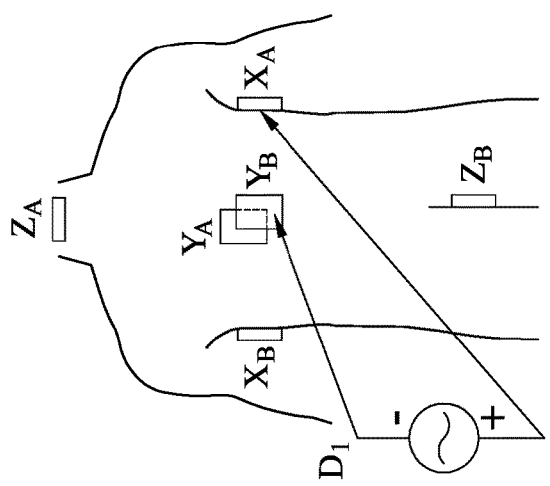
Figure 2C:
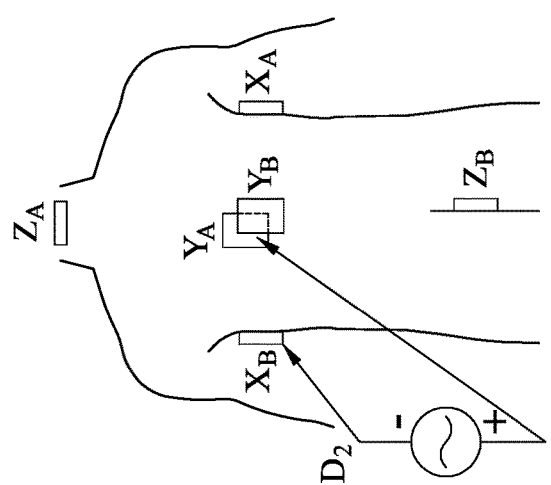
Figure 2D:
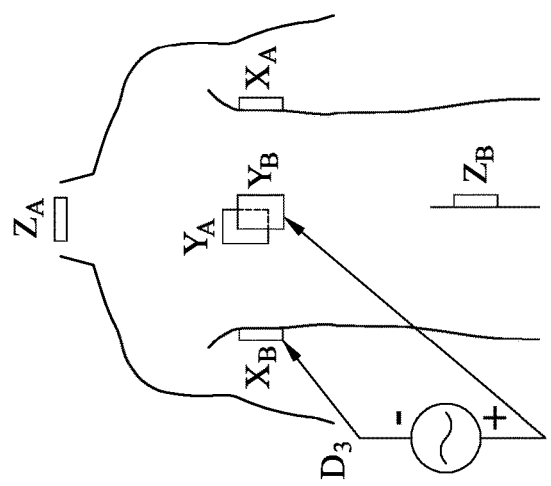

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

It can be desirable to monitor and/or control the temperature of ablation electrode assemblies. It can also be desirable to use ablation electrode assemblies to provide irrigation fluid during RF ablation. RF ablation catheters can be configured to provide temperature feedback during RF ablation via a thermal sensor such as a thermocouple or thermistor. Typically, the temperature reading provided by a single thermal sensor inside an irrigated tip ablation electrode cannot accurately represent the temperature of the electrode/tissue interface. One reason is because a portion of the electrode that is in direct contact with the targeted tissue can have a higher temperature than the interior of the electrode where a single thermocouple typically resides because tip irrigation forms a thermal gradient from the tip external surface to the tip interior.

Secondly, even properly knowing the surface interface temperature of the tip/tissue interface, the irrigation fluid can cause at-least the near surface of the target tissue to be subcooled relative to deeper tissues beyond the reach of the cooling effect but still within the RF affected heated zone. Thus the hottest spot of an irrigated lesion can be below the target tissue surface by a millimeter or two. So for better thermal control one can at-least get rid of the in-tip temperature gradient error such as by placing the thermocouple on the tip exterior surface as this invention teaches. The in-tissue temperature gradient which remains may be modeled or estimated such as by this disclosure.

Thus, if the tip thermal sensor is in direct contact with the targeted surface tissue such as by being situated on a tip surface facing that tissue, then the thermal sensor can provide a temperature reading generally corresponding to the actual temperature of the targeted tissue surface albeit that surface temperature is still suppressed by irrigation-cooling relative to deeper subsurface tissue within the RF treatment zone as stated above. Furthermore, multiple thermal sensors positioned at different tip surface locations on the electrode can be used to assure that at least one of them is directly facing the juxtaposed tissue to be lesioned no matter the rotational state of the tip relative to the tissue. For example and without limitation, the highest measured temperature of all these temperature sensing locations is likely the one facing the ablating tissue.

The ability to assess lesion formation during ablation is a desirable feature. This is achieved in today's practice by monitoring electrograms (EGM's) and pacing from electrodes before, during and after RF ablation. Closely spaced electrodes, either at or near the ablation tip can potentially provide highly local information that can be used to assess the effectiveness of the ablation therapy. That is to say that multiple electrodes facing a lesion on a catheter tip can be employed as bipolar pairs such that the electrical impedance between such nearby pairs and thereby also selectively through the intervening adjacent target-tissue and resulting lesion itself can be measured. The additional sensing electrodes can also be used to individually characterize the electrophysiology of the local substrate. This can help to diagnose the arrhythmia, determine the site for ablation and judge the resulting lesion size/depth.

FIG. 1 is a diagrammatic depiction of an exemplary intracardiac mapping and navigation system 10 for use with various medical devices that are capable of utilizing an ablating catheter electrode assembly with dual-mode, omni-directional feedback capabilities of the present disclosure. Dual-mode, omni-directional feedback capabilities can comprise thermal and electrical sensing modes that include temperature and calorimetry. Dual-mode, omni-directional feedback capabilities can further include pacing, impedance, and omnipolar electrograms as described herein. In other embodiments, dual-mode, omni-directional feedback capabilities can refer to electrograms and impedance sensing, extending the single mode electrogram approach of OIS as described herein. The system 10 may include various visualization, mapping and navigation components as known in the art, including, for example, an EnSite™ Velocity™ system commercially available from St. Jude Medical, Inc., or as seen generally, for example, by reference to U.S. Pat. No. 7,263,397, or U.S. Pat. No. 7,885,707, both of which are hereby incorporated by reference in their entireties as though fully set forth herein. With reference to the present disclosure, the system 10 is configured to, among other things, collect cardiologic data, particularly impedance and temperature information, from intra-tip electrodes and sensors, respectively, mounted to the medical device to thereby provide accurate, reliable and complimentary lesion information without regard to the orientation of the medical device. Such information can be used to perform real-time lesion assessment, in addition to providing orientation independent mapping. Further discussion of orientation independent mapping can be found in PCT Application no. PCT/US2014/037160, filed 7 May 2014 (the '160 reference), PCT Application no. PCT/US2015/017576, filed 25 Feb. 2015 (the '576 reference), and PCT Application no. PCT/US2015/017582, filed 25 Feb. 2015 (the '582 reference), which are each incorporated by reference in their entirety as though fully set forth herein. As such, users of the system 10, such as clinicians, doctors, or cardiologists, may be able to more readily perform ablation procedures for remedying cardiac arrhythmia.

The system 10 may include an electronic control unit (ECU) 12, an analog-to-digital converter (A-to-D) 14, a low-pass filter (L.P.) 16, a switch 18, a signal generator 20, and a plurality of body surface patch electrodes 22. The system 10 may be electronically and/or mechanically coupled with an elongate medical device, such as, in one embodiment, a contact or non-contact mapping catheter (e.g., a cardiac mapping catheter 24). The catheter 24 includes a distal end portion 26 and a proximal end portion 28. The distal end portion 26 includes an electrode assembly 32 and extends into a heart 36 of a patient 38. The proximal end portion 28 connects the catheter 24 to a switch 18 and to an irrigation pump (not shown).

The system 10 may be configured to provide, among other things, mapping of patient tissue, such as one or more chambers of the heart 36 of the patient 38, and a 3D model bearing the surface geometry of the mapped cardiac tissue. Accordingly, the ECU 12 may be configured to receive electrical measurements from one or more electrodes coupled to the electrode assembly 32 on the mapping catheter 24 and, based on those measurements, to assess one or more electrical characteristics of tissue surrounding the distal end of the mapping catheter 26. In an embodiment, the ECU 12 may be configured to determine a voltage distribution of an endocardial surface according to electrical measurements from mapping catheter electrode assembly 32. The ECU 12 may be further configured to determine that voltage distribution with respect to an anatomical model, such as a model of one or more chambers, features, and/or surfaces of the heart 36.

The ECU 12 may include a non-volatile memory 40 and a processor 42 configured to perform many of the functions and operations described herein—i.e., a memory 40 may store instructions for performing portions of one or more methods or processes described herein, and a processor 42 may be configured to execute those instructions to perform the methods or processes. The memory 40 may also be configured to store an anatomical model, such as a cardiac chamber model, a plurality of measurements from the mapping catheter 24, a plurality of terms and values for the methods described below, and other data and information. In an embodiment, the ECU 12 may additionally or alternatively comprise a field-programmable gate array (FPGA) and/or other known computing device. In some embodiments, and as discussed further below, the ECU 12 may be configured to perform a method of computing a 2D projection and/or a partially unfolded surface of a 3D model in order to better facilitate visualization of the model and features of the model. The ECU may also include models of the impedance behavior or heat-flow (calorimetry) behavior of forming lesions.

In addition to (and as a part of) electrophysiology mapping, the system 10 may be configured to determine the position and orientation (P&O) of the mapping catheter 24 (e.g., particularly of the distal end portion 26) within the patient 38. Accordingly, the ECU 12 may be configured to control generation of one or more electrical fields and determine the position of one or more electrodes (e.g., the electrode assembly 32) within those fields. The ECU 12 may thus be configured to the control signal generator 20 in accordance with predetermined strategies to selectively energize various pairs (bipoles) of the body surface patch electrodes 22, as described in greater detail below. In operation, the ECU 12 may (1) obtain raw patch data (i.e., voltage readings) via the filter 16 and the A-to-D converter 14 and (2) use the raw patch data (in conjunction with electrode measurements) to determine the raw, uncompensated, electrode location coordinates of the electrode assembly 32 positioned inside the heart 36 or a chamber thereof in three-dimensional space. The ECU 12 may be further configured to perform one or more compensation and adjustment functions, and to output a location of the electrode assembly 32. Motion compensation may include, for example, compensation for respiration-induced patient body movement, as described in U.S. Publication No. 2012/0172702, which is hereby incorporated by reference in its entirety for all purposes.

The body surface patch electrodes 22 may be used to generate axes-specific electric fields within the patient 38, and more specifically within the heart 36. Three sets of patch electrodes may be provided: (1) electrodes $22_{X1}$, $22_{X2}$, (X-axis); (2) electrodes $22_{Y1}$, $22_{Y2}$, (Y-axis); and (3) electrodes $22_{Z1}$, $22_{Z2}$, (Z-axis). Additionally, a body surface electrode ("belly patch") 22B, may be provided as an electrical reference. Other surface electrode configurations and combinations are suitable for use with the present disclosure, including fewer electrodes 22, more electrodes 22, or different physical arrangements, e.g. a linear arrangement instead of an orthogonal arrangement.

Each patch electrode 22 may be independently coupled to the switch 18, and pairs of the patch electrodes 22 may be selected by software running on the ECU 12 to couple the patch electrodes 22 to the signal generator 20. A pair of electrodes, for example the Z-axis electrodes $22_{Z1}$, $22_{Z2}$, may be excited by the signal generator 20 to generate an electrical field in the patient 38 and, more particularly, within the heart 36. In one embodiment, this electrode excitation process occurs rapidly and sequentially as different sets of the patch electrodes 22 are selected and one or more of the unexcited surface electrodes 22 are used to measure voltages. During the delivery of the excitation signal (e.g., current pulse), the remaining (unexcited) patch electrodes 22 may be referenced to the belly patch 22B and the voltages impressed on these remaining electrodes 22 may be measured. In this fashion, the patch electrodes 22 may be divided into driven and non-driven electrode sets. The low pass filter 16 may process the voltage measurements. The filtered voltage measurements may be transformed to digital data by the analog to digital converter 14 and transmitted to the ECU 12 for storage (e.g. in the memory 40) under the direction of software. This collection of voltage measurements may be referred to herein as the "patch data." The software may have access to each individual voltage measurement made at each surface electrode 22 during each excitation of each pair of surface electrodes 22.

The patch data may be used, along with measurements made at the electrode assembly 32, to determine a relative location of the electrode assembly 32. The patch data may also be used along with measurements made at the electrode assembly 32 and/or other electrodes on the catheter 24, such as a tip electrode, or on another device to determine a relative location of the electrode assembly 32 and/or the other electrodes. The discussion above and below describes determining the location of the electrode assembly 32, but it should be understood to apply to a tip electrode and other electrodes, as well. In some embodiments, potentials across each of the six orthogonal patch electrodes 22 may be acquired for all samples except when a particular surface electrode pair is driven. In some embodiments, sampling a voltage with a particular patch electrode 22 while a surface electrode 22 acts as a source or sink in a driven pair may be avoided, as the potential measured at a driven electrode during this time may be skewed by the electrode impedance and the effects of high local current density. In an alternate embodiment, however, sampling may occur at all patch electrodes 22, even those being driven.

Generally, in an embodiment, three nominally orthogonal electric fields may be generated by a series of driven and sensed electric bipoles in order to determine the location of the catheter 24 (i.e., of the electrode assembly 32). Alternately, these orthogonal fields can be decomposed and any pair of surface electrodes (e.g., non-orthogonal) may be driven as bipoles to provide effective electrode triangulation.

FIGS. 2A-2D show a plurality of exemplary non-orthogonal bipoles, designated $D_0$, $D_1$, $D_2$ and $D_3$. In FIGS. 2A-2D, the X-axis surface electrodes are designated $X_A$ and $X_B$, the Y-axis surface electrodes are designated $Y_A$ and $Y_B$, and the Z-axis electrodes are designated $Z_A$ and $Z_B$. For any desired axis, the potentials measured across an intra-cardiac electrode assembly 32 resulting from a predetermined set of drive (source-sink) configurations may be combined algebraically to yield the same effective potential as would be obtained by simply driving a uniform current along the orthogonal axes. Any two of the patch electrodes 22 may be selected as a bipole source and drain, as noted above, with respect to a ground reference, e.g., the belly patch 22B, while the unexcited body patch electrodes 22 measure voltage with respect to the ground reference. The electrode assembly 32 placed in the heart 36 is also exposed to the field from a current pulse, and voltages on electrode assembly 32 are individually and separately measured with respect to ground, e.g., the belly patch 22B.

Referring again to FIG. 1, data sets from each of the patch electrodes 22 and the electrode assembly 32 are all used to determine the location of the electrode assembly 32 within the heart 36. After the voltage measurements are made for a particular set of driven patch electrodes 22, a different pair of patch electrodes 22 may be excited by the signal generator 20 and the voltage measurement process of the remaining patch electrodes 22 and the electrode assembly 32 takes place. The sequence may occur rapidly, e.g., on the order of one hundred times per second in an embodiment. To a first approximation the voltage on the electrode assembly 32 within the heart 36 bears a linear relationship with position between the patch electrodes 22 that establish the field within the heart 36, as more fully described in U.S. Pat. No. 7,263,397 referred to above.

Some or all of the conventional twelve (12) ECG leads, coupled to additional body patches and designated collectively by reference numeral 44, may be provided to support the acquisition of an electrocardiogram (ECG) of the patient. As shown, the ECG leads 44 may be coupled directly to the ECU 12 for acquisition and subsequent processing to obtain the phase of the heart in the cardiac cycle. Cardiac phase information may be used, in an embodiment, in mapping of electrical activity of the heart 36, as described below.

In summary, FIG. 1 shows an exemplary system 10 that employs seven body patch electrodes 22, which may be used for injecting current and sensing resultant voltages. Current may be driven between two patches 22 at any time. Measurements may be performed between the non-driven patch 22 and, for example, the belly patch 22B as a ground reference. A patch bio-impedance, also referred to as a "patch impedance", may be computed according to the following equation:

$$BioZ[n \to m][k] = \frac{V_k}{I_{n \to m}}$$

where $V_k$ is the voltage measured on patch k and $I_{n \to m}$ is a known constant current driven between patches n and m. The position of the electrode assembly 32 may be determined by driving current between different sets of patches and measuring one or more patch impedances. In one embodiment, time division multiplexing may be used to drive and measure all quantities of interest. Position determining procedures are described in more detail in, for example, U.S. Pat. Nos. 7,263,397 and 7,885,707 referred to above. To perform an electrophysiology (e.g., mapping) procedure, the distal end portion 26 of the catheter 24 or multiple such catheters 24 may be manually guided to a desired location by a user such as a physician.

In addition to determining the positions of the electrode assembly 32, the system 10 may also be configured to characterize and assess the tissue of the heart, including lesions. Accordingly, the ECU 12 may be further configured to perform one or more steps in one or more complimentary methods of determining a voltage distribution on a cardiac surface, such as determining the impedance between intra-tip electrodes facing the lesion and sensing the temperature at multiple locations facing the lesion on electrode assembly 32. Because these methods employ entirely different signal types (electrical voltage and temperature) they provide a more sound answer as to lesion size by using two entirely independent lesion-assessment mechanisms. In the case of the temperature aspect, the use of temperature sensing over time can be used in response to an RF power change. The temporal temperature response can be fitted to a thermal model of the tissue in manners of thermal modeling both inside and outside catheter ablation. One embodiment employs the intra-tip impedance measurements and the complimentary and independent temporal temperature responses to RF power changes (which temporal responses are referred to as thermal calorimetry). Both pieces of information can be utilized such as by averaging them or weighing one somewhat more than the other in accordance with the user's confidence in each.

Figure 3:
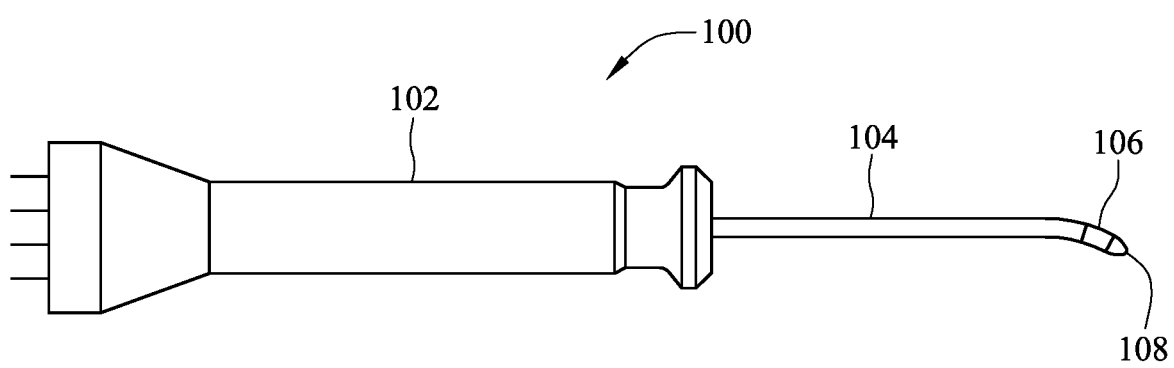
FIG. 3 is a schematic diagram of one embodiment of a medical apparatus incorporating an electrode assembly.

FIG. 3 illustrates a schematic diagram of a medical apparatus incorporating an electrode assembly as described below. In the illustrated embodiment, the medical apparatus can comprise a catheter 100. The catheter 100 can comprise a control handle 102, and an elongated catheter body 104 having a distal region 106 with an electrode assembly 108. The distal region 106 can comprise any of the catheter tips shown and described below. The catheter 100 can be connected to an ECU as described below.

In one embodiment, the electrode assembly discussed herein can comprise a multi-electrode RF ablator tip having dual-mode (the bipolar electrical impedance mode and the complimentary independent calorimetry mode embodiment discussed above) omnidirectional lesion feedback capability, mapping and orientation independent sensing capability and optionally shared interconnects. An electrode tip assembly as discussed herein can have these characteristics while still leaving physical room for a force feedback sensor. Lesion feedback can be assessed omnidirectionally, this means the catheter tip is able to be used to acquire information with any rotational orientation or regardless which tip surface is actually facing the cardiac tissue, using one or both complimentary feedback methods (both simultaneously, sequentially, or independently used) practiced from a multi-electrode tip with an electrically-insulative substrate. As a result, in some embodiments, no rotation of the electrode tip is required to ensure that the minimum needed tissue-facing electrodes (for lesion impedance feedback) and thermocouples (for lesion thermal or calorimetric feedback) are, by-default, always facing the tissue of interest.

To explain further, two different methods can be used together, either simultaneously or sequentially in a complimentary fashion, to provide more reliable lesion feedback than previous methods. The first method is in-tip cross-electrode (bipolar) or single electrode (unipolar) electrical impedance measurement(s). Bipolar measurements can be done using one or more in-tip subelectrode pairs, with the utilized bipolar-driven pair facing the lesion and showing the major known local impedance changes accompanying lesion formation. An RF body patch is not required for these lesion-local measurements and the real time local temperature can be taken into account as it has a known effect on impedance also. Unipolar measurements can be done using a 3-termial impedance measurement. These two methods can result in more specific ablation or pacing segment activation. The second complimentary and independent method is "calorimetry" which can comprise monitoring real time local surface-tissue lesion temperature in response to a known ablation energy input rate changes (input rate increases or decreases such as momentary turning on or off of power) injected into an assumed model-volume of tissue of known thermal properties adjacent the known electrodes. Another method to change (e.g. momentarily reduce) effective heat energy input is to change (e.g. momentarily reduce) the irrigant flow rate which essentially leaves more heat in the lesion tissue region.

In this second calorimetry method a simple thermal model of the tissue (temperature versus depth) is employed. Essentially widely known tissue thermal models can predict the buildup or relaxation of a temperature-vs depth profile as a function of time after a heat input at the tissue surface is started or stopped. Other than the input lesion energy and irrigant heat removal the other assumptions that can be made are that the initial tissue is at 37 Deg C (body temperature) and that the target tissue is blood-perfused (further cooled by perfusing blood). Thus, since we can detect the tissue surface temperature and we can predetermine at what time ablating heat (or irrigation) is turned on or off or step-changed in magnitude, we can observe the changing surface temperature upon such a heating change and deduce a lesion temperature depth profile and lesion tissue thermal conductivity versus depth during that observation period. There is a unique solution for the temperature and thermal conductivity profile for each observed surface temperature response to a heating change. Thus knowing the deduced temperature profile and thermal conductivity profile allows judgement of the lesion extent based purely on thermal considerations. For example lesioned tissue has markedly lower thermal conductivity than unlesioned tissue. For example the presence of a high temperature (e.g 60 deg C.) at a known depth allows an estimate of the time-to-necrosis to be estimated (less than a second to necrosis at 60 deg C.). Further discussion relating to thermal models can be found in Berjano, Enrique J., Theoretical modeling for radiofrequency ablation: state-of-the-art and challenges for the future, BioMedical Engineering OnLine 2006, 5:24, which is hereby incorporated by reference as though fully set forth herein.

In one embodiment, the tip can have a thermally and electrically-insulative substrate such as a ceramic substrate and a plurality of thin electrodes on an outside substrate surface such that the thermal response of the tissue results in the thin metal surface electrode portions, and any thermally connected thermal sensors, closely and rapidly follow the detectable tissue surface temperature. By placing thermal sensors around the tip such as under small isolated discs of such thin film electrodes, the thermal sensors can measure that tissue surface tissue temperature in real time because those thermal sensors have a thermally insulating base, i.e. a ceramic base, and virtually no depth-wise or lateral heat transfer. In ceramic tips of low thermal conductivity, the tip can have a significant irrigant flow (recirculating or passed into the bloodstream) to maintain tip surface temps below blood thrombosis temperatures. Alternatively or additionally the tips can ablate in a pulsed RF mode wherein time is allowed for the tip surfaces to cool between such repeated ablation power pulses.

In some embodiments, the thermal sensor (e.g thermocouple or thermistor) wires and the isolated disc sub-electrode wires can be cross-shared to perform one or more of the following: tissue temperature measurement, tissue impedance measurement, tissue electrical potential mapping or pacing, and electric-field spatial navigation or even ablation itself. Since these embodiments can optionally perform several functions with very few wires, thereby retain compatibility with tip-force sensor usage by limiting the required space for wired interconnections within the catheter body and catheter tip and reserving space for a tip-force sensor which has its own interconnections. The tip electrodes, as described above and below, can take on a range of configurations ranging from several large electrodes with small gaps to a single large electrode with smaller separate electrically isolated electrodes embedded in it. The actual ablation electrodes may or may not be shared or included in the feedback electrodes. In one embodiment, it is desired to have the feedback electrodes and the feedback thermal sensors provide lesion-specific feedback which means that the feedback electrodes and thermal sensors will be within the area-wise confines of the ablating electrode.

The tip electrodes described herein can lead to reduced manufacturing costs. The ceramic tips can be precisely green-molded and then fully fired to have fine features and surface finishes and even electrical and irrigant vias or ports to route interconnections and/or irrigant from the tip interior to the tip outer surfaces. The metallization of the electrode tips can be done in several different ways depending on the desired product and cost. In one embodiment, the ceramic tip substrates can comprise one of aluminum oxide (alumina) or zirconium oxide (zirconia) or zirconia toughened alumina. In one embodiment, all of the metallization processes can be batched and several hundred electrode tips can be co-deposited. The metallization techniques can include one or more of wet plating, PVD, and CVD vapor deposition methods for metals such as platinum or other exposed noble metals. The patterned electrodes can also be patterned additively or subtractively. A modified laser developed for machining stents can be used to pattern the narrow kerfs through a metallic ceramic overcoat to define such separated electrodes down to an underlying isolating ceramic base layer. An exemplary method such as sputtering may be used to deposit a well-adhering underlayer and then a second process such as electroplating may be used to thicken the electrode at a much lower processing cost. Subtractive etching or lasering might be done on the underlayer or on the dual layer sandwich. Screen printing or other mechanical printing methods for surface film conductors can be used if the needed electrode pattern resolution is loose enough. Inkjet printing of conductor films can likewise be used.

Vias or irrigant ports may be molded or drilled into the ceramic tips such that interconnections from the surface electrodes can be routed into the tip interior and irrigant may pass outwards from the tip. Those via interconnections might electrically and physically comprise plated vias or discrete wires routed through the vias. Presuming the vias are metallized or plated, at least near their outside tip-surface as by electroless plating, electroplating, CVD or sputtering for example, then the metallurgical joint between a discrete via wire and the via metallization can be hidden beneath the tip surface and covered over with a localized coating or plug of biocompatible epoxy or the like. The hidden metallization joint may comprise, for example, a soldered joint, laser welded joint or a silver-epoxy joint for example. In another embodiment, a via/port can deliver both irrigant and route an electrode or thermocouple interconnection to the tip surface.

Figure 4:
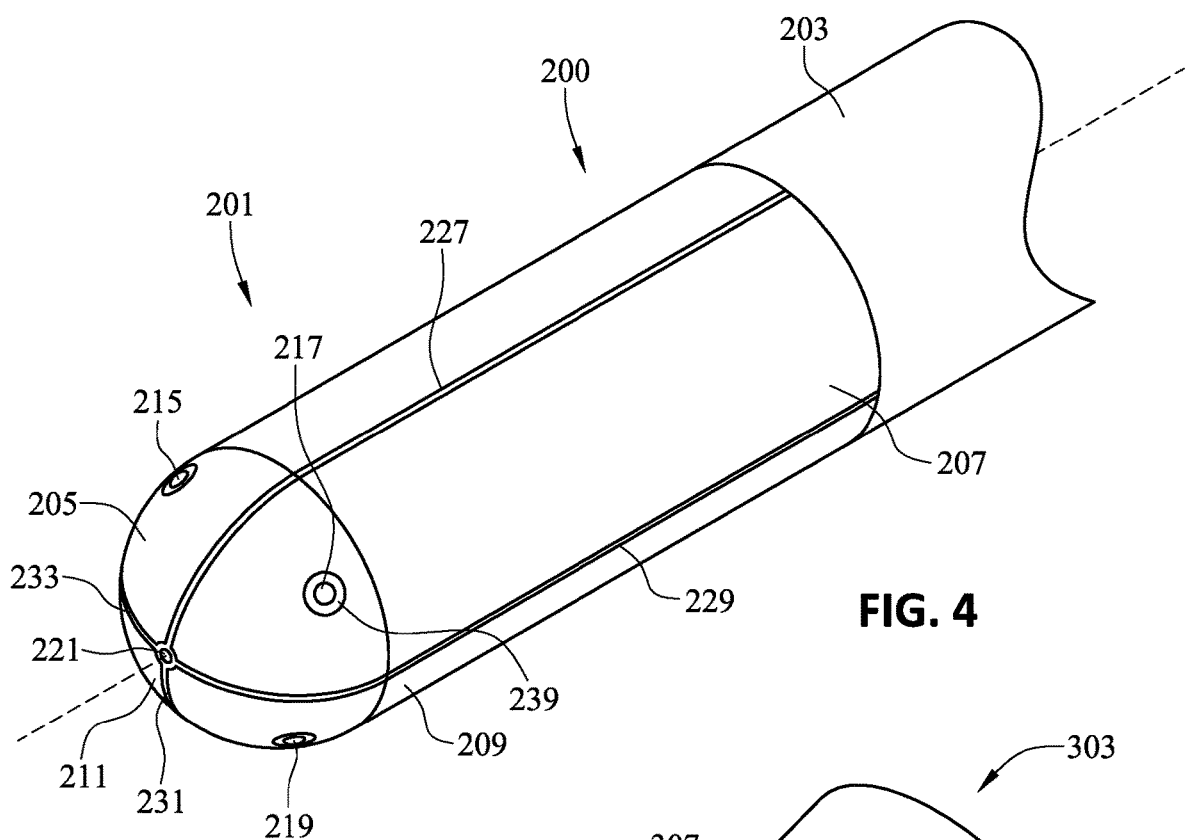
FIG. 4 is an isometric view of an embodiment of a catheter assembly comprising a plurality of segmented tip electrodes and a plurality of spot electrodes.

An embodiment of a catheter assembly 200 is generally shown in FIG. 4. The catheter assembly 200 can comprise a tip electrode group 201 and a catheter shaft 203. In the illustrated embodiment, the tip electrode group 201 can comprise a first segmented tip electrode 205, a second segmented tip electrode 207, a third segmented tip electrode 209, a fourth segmented tip electrode 211, a first spot electrode 215, a second spot electrode 217, a third spot electrode 219, a fourth spot electrode (not shown), an irrigation through-hole 221, a first exposed non-conductive segment 227, a second exposed non-conductive segment 229, a third exposed non-conductive segment 231, and a fourth exposed non-conductive segment 233. Each of the plurality of spot electrodes can be separated from other conductive portions of the tip electrode group 201 by a spot non-conductive portion 239. In the illustrated embodiment, each of the plurality of spot electrodes 215, 217, 219 is generally circular in shape and the spot non-conductive portion that surrounds each of the plurality of spot electrodes is generally circular in shape. Each of the plurality of spot electrodes can further be coupled to a thermal sensor. The thermal sensor can comprise a thermistor, a thermocouple, or other thermal sensor as would be known to one of skill in the art. In one embodiment, the thermal sensor can be electrically and thermally coupled to the spot electrode. In another embodiment, the spot electrode can comprise a thermal sensor. In one embodiment, the spot non-conductive portion 239 is of equal diameter around each of the spot electrodes. The plurality of non-conductive segments can be of equal diameter around each of the spot electrodes. The non-conductive segments can comprise various methods of separating the electrodes via a process such as one or more of the above mentioned subtractive or additive processes. In some embodiments, the non-conductive segments can comprise electrode-layer gaps between adjacent electrodes. In one such embodiment, the gap between adjacent electrodes can comprise an exposed portion of an inner electrically-insulative ceramic substrate of the tip electrode. In another such embodiment, the gap can comprise an electrically and thermally insulative ceramic material. In another such embodiment, the gap can comprise an electrically or thermally insulative material. The catheter assembly 200 can comprise part of an irrigated or non-irrigated catheter system for examination, diagnosis, and/or treatment of internal body tissues (e.g. targeted tissue areas). In an exemplary embodiment, the catheter assembly 200 can comprise an ablation catheter (e.g. radio frequency (RF), cryoablation, ultrasound, etc.). The instant disclosure refers to RF ablation electrodes and electrode assemblies, but it is contemplated that the instant disclosure is equally applicable to any number of other ablation electrodes and electrode assemblies. The vias mentioned above can be routed to the spot electrodes 215, 217 and/or to the larger electrodes 205, 207. In FIG. 4 the vias are not visible as they are hidden by their overlying surface electrodes or by the above-mentioned via plug material. In any event such vias can be used to route surface connections to the tip interior through the tip wall thickness.

The tip electrode group 201 can comprise multiple segmented tip subelectrodes that can be configured to perform directed ablation toward selected tissue, and the spot electrodes can act not only as localized thermal sensors, but can also act as electrodes for locally sensing or pacing tissue, measuring local impedance such as between different spot electrodes. The spot electrodes can also further be configured to act as e-field navigation electrodes. The spot electrodes can further be used with the segmented tip electrodes of the tip electrode 201 for orientation independent sensing as described in the '160 reference, the '576 reference, and the '582 reference incorporated by reference above. In one embodiment, where a conductor pair coupled to the thermal sensor is electrically connected to a spot electrode, the shared functions as described herein can be used to decrease the total number of wires within the tip electrode. In another embodiment, the tip electrode can comprise five segmented tip electrodes around the tip circumference. The five segmented tip electrodes can be used such that an assumption can be made that at least two of the segmented tip electrodes and associated spot electrodes face tissue for a majority of their longitudinal length. In some embodiments, the larger electrodes surround smaller or spot electrodes as shown in FIG. 4. However, in other embodiments, the smaller or spot electrodes are not surrounded by larger electrodes. In further embodiments, an electrode overlaying the distal tip comprise can comprise one contiguous electrode. A common feature of the preferred embodiments herein is that vias can be employed through the ceramic tip material to route interconnections from the tip outer surface to an interior hollow core of the tip such that such interconnections may pass out of the tip proximally toward the catheter control handle as discrete wires or flex circuit traces. In some embodiments, the vias are metallurgically coupled to tip-interior discrete wires or flex circuit traces in a manner wherein any nonbiocompatable metallurgy or conductive epoxy employed to electrically join the vias and wires or traces is masked or hidden from blood exposure at the tip outer surface. In one embodiment, at least one of the vias can serve as an irrigation port and some irrigation ports disposed within the tip can have no electrical interconnection function.

In another embodiment, the spot non-conductive portions can be removed or filled such that an individual segmented tip electrode and the associated spot electrode can be thermally and electrically coupled. As a result, the thermal sensor and associated spot electrode cannot be used as a separate electrode from the segmented tip electrode, however, the thermal sensor can still be used for calorimetry purposes. Calorimetry is the monitoring of the temperature of a tissue mass during calibrated heat-input or heat-output such that a thermal property of the tissue mass can be deduced.

In simplest terms, as a tissue dehydrates and lesions develop, the tissue's thermal conductivity and specific heat drop significantly. As a result, a pulse of injected heat before such a lesion is made will result in a smaller depth-wise temperature gradient than after the lesion is present and cooled back to a starting temperature. Use of the disclosure can involve calorimetry measurement before, during, and after a lesion is formed when the calorimetry method is employed. Tissue impedance can be a function of tissue dehydration but also of tissue temperature. Thus measuring such temperature facing the lesion also results in a more accurate temperature-corrected lesion impedance reading. Given a pair of electrodes or spot electrodes which both face tissue, the bipolar impedance can be measured between such pairs of intra-tip electrodes. This impedance can be affected by the electrode spacing, which will determine the penetrating depth of fringe fields, and electrode size which is fixed and can be a design choice. The two techniques, bipolar impedance lesion feedback and calorimetry each depend on different lesion physical properties-i.e. electrical conductivity versus thermal conductivity/specific heat. The electrical impedance depends primarily on the electrical conductivity of the lesion and has a depth limit dictated by the shape of the electrical fringing fields whereas thermal calorimetry depends on the thermal conductivity and specific heat of tissue and has a deeper depth limit from which residual heat may leak toward the tissue surface. Thus, complimentary techniques can improve accuracy.

Figure 5:
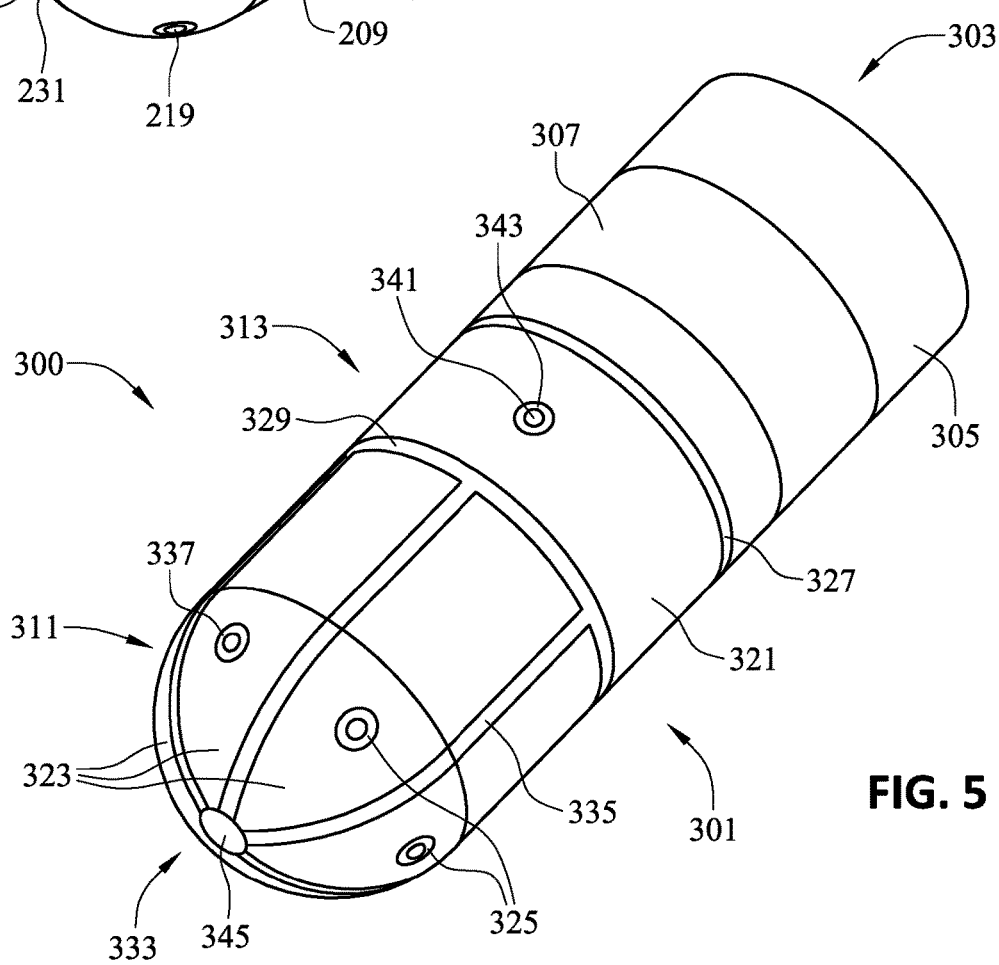
FIG. 5 an isometric view of another embodiment of a catheter assembly comprising a plurality of segmented tip electrodes and a plurality of spot electrodes.

FIG. 5 depicts an isometric view of another embodiment of a catheter assembly 300. The catheter assembly 300 can comprise a tip electrode group 301 and a catheter body 303. The catheter body can comprise a catheter shaft 305 and a ring electrode 307. The ring electrode 307 can be coupled to a distal portion of the catheter shaft 305. The tip electrode group 301 can comprise a distal electrode portion(s) or subelectrodes 311 and a proximal portion(s) or subelectrodes 313. In the illustrated FIG. 5 embodiment, the proximal portion 313 can comprise a mostly cylindrical single electrode shape, and the distal portion 311 can comprise a rounded dome. In the depicted case the distal dome electrode 311 portion(s) comprises five separate subelectrodes around the circumference. Thus the tip electrode or electrode group 301 can comprise a plurality of individual electrodes or electrode subgroups. The type and placement of the individual electrodes on the tip electrode can vary depending on the desired use of the tip electrode or other design reasons. In the illustrated FIG. 5 embodiment, the tip electrode 301 can comprise a proximal tip ring electrode 321, a plurality of distal segmented subelectrodes 323, and a plurality of spot electrodes 325, 341. The tip ring electrode 321 in the illustrated embodiment is located on a proximal portion 313 of the tip electrode 301. Each of the individual electrodes of the tip electrode 301 can be separated from other electrically conductive portions of the tip electrode and the ring electrode by a non-conductive portion or gap in the deposited electrode layer upon the electrically insulating ceramic substrate. In the illustrated FIG. 5 embodiment, the tip ring electrode 321 can be bordered by a first circumferential non-conductive gap portion 327 at a proximal end of the tip ring electrode 321 and a second circumferential non-conductive gap portion 329 at a distal end of the tip ring electrode 321. The gap portions 327, 329 comprise exposed electrically insulating tip ceramic substrate material for example. Such gap portions may comprise lasered gaps in the electrode layer. In other embodiments one or both of the circumferential non-conductive portions can be removed from the catheter assembly.

A plurality of subelectrodes 323 can also be located on the catheter assembly 300. Each of the subelectrodes 323 can be separated from the tip ring electrode and other subelectrodes by a non-conductive gap portion of the tip electrode 301. In the illustrated embodiment, each of the segmented subelectrodes can extend longitudinally from the second circumferential non-conductive portion 329 to a distal end 333 of the tip electrode 301. In the illustrated embodiment, each of the plurality of segmented subelectrodes 323 can be separated by a longitudinally extending non-conductive gap portion 335. FIG. 5 illustrates a tip electrode with 6 discrete longitudinally extending non-conductive gap portions delineating six separate segmented subelectrodes. Other embodiments of a tip electrode according to this disclosure can have varying numbers of longitudinally extending non-conductive portions and varying numbers of segmented electrodes. The tip electrode 301 can further comprise a plurality of spot electrodes 325. In the illustrated embodiment of FIG. 5, an individual spot electrode is disposed within each of the segmented tip subelectrodes and can be located on and equally spaced around the distal portion 311 of the tip electrode 301. Each of the plurality of spot electrodes 325 can be surrounded by a spot non-conductive portion 337. The spot non-conductive portion 337 can electrically isolate each of the spot electrodes from the rest of the tip electrode 301. Note that both the spot electrodes and larger surrounding electrodes are both situated upon the electrically insulating tip substrate material. In other embodiments, the spot electrodes can be in other configurations. In one embodiment, each of the spot electrodes can be located on the proximal portion of the tip electrode 301 and can also be evenly spaced around an outer circumference of the tip electrode 301. In another embodiment, each of the spot electrodes can be located adjacent the segmented tip electrodes. In other embodiments, each of the spot electrodes can be located within the longitudinal non-conductive portion of the tip electrode. In on embodiment, each of the spot electrodes can be located within the longitudinal non-conductive portion of the tip electrode and each of the spot electrodes can be further surrounded by a spot non-conductive portion.

The tip electrode can further comprise at least one ring spot electrode 341. The at least one ring spot electrode 341 can be disposed within the tip ring electrode 321. In the illustrated embodiment, the at least one ring spot electrode 341 can be disposed evenly between a proximal edge of the tip ring electrode and a distal edge of the tip ring electrode. The at least one ring spot electrode 341 can be surrounded by a ring spot non-conductive portion 343. The ring spot non-conductive portion 343 can electrically isolate the ring spot electrode 341 from the tip ring electrode 321 and can also electrically isolate the ring spot electrode 341 from the rest of the electrodes on the tip electrode 301. In other embodiments, the at least one ring spot electrode can comprise a first ring spot electrode and the electrode tip can comprise additional ring spot electrodes spaced apart from the first ring spot electrode. In one embodiment, the tip electrode can comprise a second ring spot electrode disposed around 180 degrees around a circumference of the tip ring electrode from the first ring spot electrode. In another embodiment, the tip electrode can comprise four separate ring spot electrodes evenly spaced at 90 degrees around a circumference of the ring electrode 321. The tip electrode 301 can further comprise one or more irrigation through-holes 345. The irrigation through-hole(s) 345 can be fluidly coupled to an irrigation source to supply an irrigant or other fluid to an exterior of the distal portion 311 of the electrode tip 301. In other embodiments, the irrigation through-hole can comprise one of a plurality of irrigation through-holes. In the illustrated embodiment, each of the longitudinally extending non-conductive portions 335 can extend from the second circumferential non-conductive portion 329 to a non-conductive portion surrounding the irrigation through-hole 345. This results in each of the segmented tip electrodes being bound on a proximal end by the second circumferential non-conductive portion 329, on each side by a separate longitudinally extending non-conductive portion, and at a distal end by the irrigation through-hole 345. In another embodiment, each of the segmented electrodes can abut the irrigation through-hole. In some embodiments, an irrigation via 345 including a metallized interior diameter metallized also is also configured to act as an electrical connection or via from the tip surface to the tip interior such as to both RF-power and irrigate a surface electrode.

Figure 6:
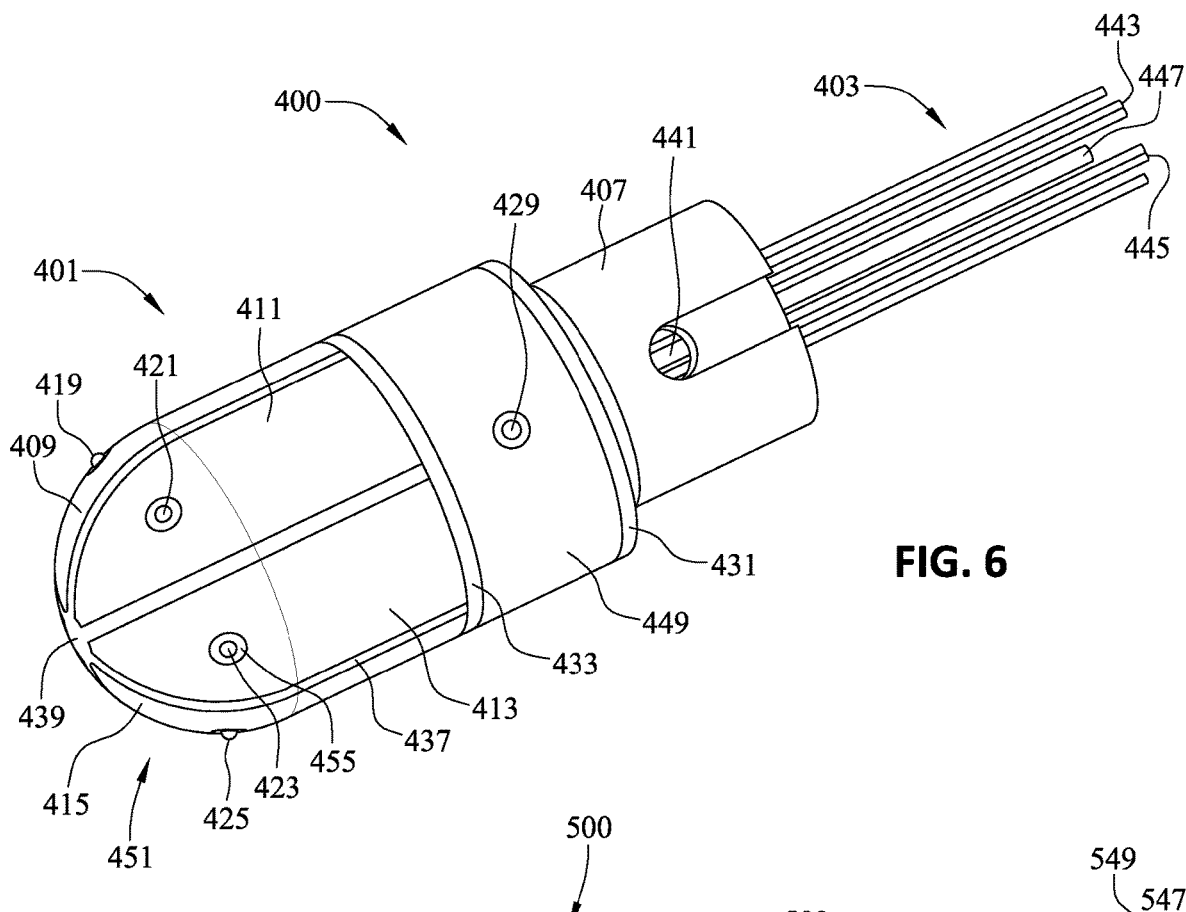
FIG. 6 is an isometric view of an embodiment of a tip assembly comprising a plurality of segmented tip electrodes and a plurality of spot electrodes.

FIG. 6 illustrates an embodiment of a tip assembly 400 comprising a tip electrode group 401 and a conductor assembly 403. The tip electrode group 401 can comprise a base portion 407, a plurality of individual electrodes and a non-conductive portion surrounding each electrode. In the illustrated embodiment, the plurality of individual electrodes can comprise a first segmented tip electrode 409, a second segmented tip electrode 411, a third segmented tip electrode 413, a fourth segmented tip electrode 415, a fifth segmented tip electrode (not shown), a sixth segmented tip electrode (not shown), a first spot electrode 419, a second spot electrode 421, a third spot electrode 423, a fourth spot electrode 425, a fifth spot electrode (not shown), a sixth spot electrode (not shown), a tip ring electrode 449, a first ring spot electrode 429, and a second ring spot electrode (not shown). The tip electrode 401 can further comprise a proximal circumferential non-conductive portion 431, a distal circumferential non-conductive portion 433, a plurality of longitudinal non-conductive portions 437, and a distal end non-conductive portion 439. Each of the segmented tip electrodes can be separated from adjacent segmented tip electrodes by one of the plurality of longitudinal non-conduction portions 437. Each of the segmented tip electrodes can extend longitudinally from the distal circumferential non-conductive portion 433 to the distal end non-conductive portion 439. The distal end non-conductive portion 439 can be disposed on a distal end 451 of the tip electrode 401. Each of the spot electrodes can be electrically and thermally isolated from the other electrodes on the tip electrode 201 by a spot non-conductive portion 455. The base portion 407 can be sized and configured to fit within a catheter body to couple the tip assembly 400 to the catheter body. The base portion 407 can further comprise a tip anchor 441. The tip anchor 441 can be used to further secure the tip assembly 400 to a catheter shaft. The conductor assembly 403 can comprise a plurality of individual conductors or conductor pairs. Each of the conductor pairs can be coupled to an individual thermocouple disposed within the tip electrode 401. Each of the conductor pairs can electrically couple one or more electrodes to a connector or other device to allow for signals to be measured from the various electrodes of the tip electrode 401 or to deliver energy through the various electrodes to a target area or tissue. In one embodiment, the thermocouple leads (one or both) can be used as interconnection wires to also power the sensing or ablating electrodes. In some embodiments, the conductor pairs can also be coupled to a thermal sensor or form a thermal sensor or thermocouple in which case the wire pair may be thermocouple alloy wires such as a copper wire and a constantin wire. This can be an example of wire-sharing where two wires form a tip-surface thermocouple but can also power a surface electrode or detect electrical signals on a surface electrode. The thermal sensors (e.g. thermocouples or thermistors having two wires) can be disposed adjacent an outer tissue exposed surface of the tip electrode and can transfer temperature and other data to a proximal end of a conductor pair. The illustrated embodiment shows at least a first conductor pair 443, a second conductor pair 445, and a third conductor pair 447. In one embodiment, a separate conductor pair is electrically connected to each of the discrete electrodes disposed on the tip electrode. In another embodiment, each of the conductor pairs can be electrically connected to one or more of the discrete electrodes disposed on the tip electrode. In another embodiment, such as that shown in FIG. 5, the conductor assembly can comprise a plurality of conductor pairs and an irrigation lumen. The irrigation lumen can be configured to be coupled to an irrigation source. It will be appreciated that with so many electrodes and thermal sensors such wire-sharing can be very beneficial.

Figure 7:
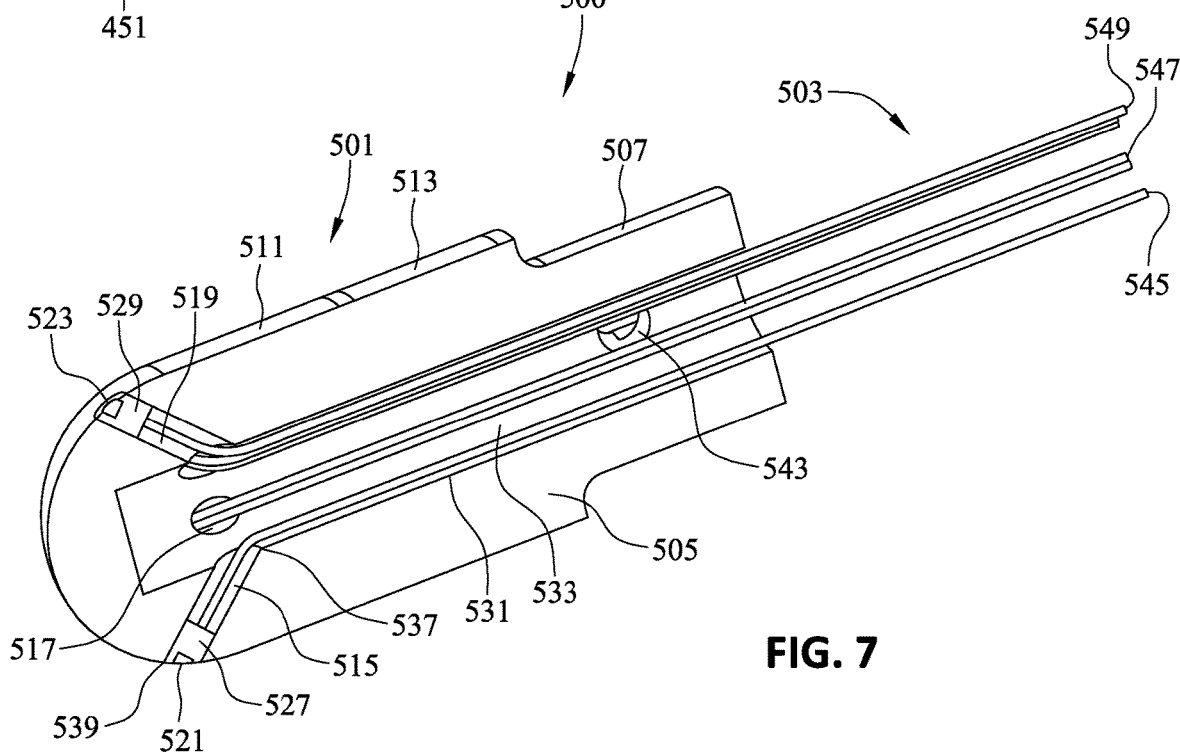
FIG. 7 is an isometric, cross-sectional view of an embodiment of a tip assembly comprising a plurality of segmented tip electrodes and a plurality of spot electrodes.

FIG. 7 illustrates an isometric, cross-sectional view, of an embodiment of a tip assembly 500 comprising a tip electrode group 501 and a conductor assembly 503. The tip has a base portion 507 and can also comprise an electrically-insulative substrate 505 and which mates with a polymer lumen. The electrically-insulative substrate 505, 507 can either be made of ceramic materials or polymers of various durometers. The electrically-insulative substrate can be an injection molded component. Injection molded describes molded with a polymer to a final shape or with a ceramic molded to a green shape which is then fired in a furnace. The electrically-insulative substrate can be formed in various configurations according to the desired use of the catheter. These configurations can include irrigation lumens, irrigation flow holes, sensor channels, and/or conductive channels (metallized electrical vias or holes for discrete wires) as well as structures for mechanical attachment, alignment, or stabilization. The conductive material can be selectively bonded to, deposited, or coated onto the electrically-insulative substrate by various techniques, including low temperature print manufacturing (with or without sintering), screen-printing, die-embossing, inkjet deposition, electroplating, electroless plating, sputter deposition, heat, mechanical deformation, cathodic arc deposition, diffusion bonding, evaporative deposition and pulsed laser deposition or combinations thereof.

The tip electrode group 501 can comprise and be formed within a thin layer of conductive material clad or deposited onto the electrically-insulative substrate 505, 507. The thin layer of conductive material deposited onto the electrically-insulative substrate can improve temperature correlation between the electrode and tissue interface because it is configured as a thin layer of heat and electrically conducting material, and itself has a low thermal capacity to modulate heat in the tissue itself. The thin metal layer on the electrically and thermally insulating substrate 505, 507 can also therefore preserve important thermal gradients seen along the tissue surface. The thin layer of conductive material (one or more electrodes thereof) can be at-least temporarily if not permanently electrically connected to an ablation system to allow for the delivery of ablative energy or the like. The thin layer of conductive material can be electrically connected to the ablation system in any manner conventional in the art. For example, a conductor wire can be provided. The conductor wire can extend through a lumen within the catheter shaft. The patient may also utilize a ground-return patch in the case of a single wire fed monopolar RF tip. Groups of such electrodes may be employed to perform ablation and/or perform impedance feedback from lesions or to perform electrical sensing or pacing.

In some embodiments the electrically-insulative substrate can comprise a thermally insulative material. Alumina, zirconia toughened alumina and zirconia are all poor thermal conductors but have been proven in dental and medical implants. Silicon nitride is a better thermal conductor than the others but still electrically insulative and also proven in medical implants. Silicon nitride has the same order of thermal conductivity as platinum iridium which is a very poor metallic thermal conductor. For this reason silicon nitride can thermally act similarly to existing platinum-iridium tips and remove substantial heat from the tissue by having the tip irrigated.

In such embodiments the electrically-insulative substrate can provide an insulated internal flow path for ionically conductive saline or other irrigation fluid. The electrically-insulative substrate can thermally isolate the multiple thermal sensors located within the tip electrode 203. By thermally isolating the temperature sensors, the tip electrode 203 can have an improved ability to measure the temperature at the tip-tissue interface during lesion formation. i.e. Using the thermally insulating substrate 505 the tip can accurately and more importantly rapidly detect the true tissue surface temperature without suppressing it to a large degree due to tip-induced tissue cooling. The listed ceramics above allow placement of temperature sensors on the tip surface.

The tip electrode group 501 of FIG. 7 can further comprise at least one segmented subelectrode 511, a tip ring electrode 513, a first via or wire channel 515, a second via or wire channel 517, a third via or wire channel 519, a first spot electrode 521, a second spot electrode (not shown), a third spot electrode 523, a first spot non-conductive portion 527, a second spot non-conductive portion (not shown), a third spot non-conductive portion 529, and an inner tip surface 531. While not shown, other electrodes can be present on the tip electrode 501 as described throughout the disclosure. The inner tip surface 531 can define an inner lumen 533 that extends from a proximal end of the tip electrode 501 to a more distal portion of the tip electrode 501. The inner lumen 533 can be configured to allow for wires, irrigation lumens, or other desired components to be placed or routed through an inner portion of the tip electrode 501. The first channel 515, the second channel 517, and the third channel 519 can extend from the inner tip surface 531 to an exterior tip surface. In the illustrated embodiment, each of the channels extends from an inner channel opening 537 to an outer surface opening 539. Each of the channels (electrical interconnection vias or water irrigation ports or both) can comprise various sizes depending on the components designed to be placed within. In the illustrated embodiments, each of the channels can comprise a cylindrical hole within the electrically-insulative substrate 505 of the tip electrode 501. In other embodiments, each of the channels can comprise other shapes and sizes as may be warranted by design considerations or ease of manufacturing. As seen in the illustrated embodiment, the inner channel opening is located proximally from the outer surface opening. This results in the outer surface opening 539 being located in a distal direction of the inner channel opening 537. In other embodiments the inner channel opening and the outer surface opening of one or more of the channels can be located along the same portion of a longitudinal axis of the tip electrode. This placement of the channel can result in a roughly 90 degree angle between the channel and the inner lumen of the tip electrode. In yet other embodiments, the inner surface opening can be located in a distal position in relation to the outer surface opening. This results in the outer surface opening being located in a proximal direction of the inner channel opening. In other embodiments, a plurality of channels located within a tip electrode can comprise one or more of the embodiments listed above. In other embodiments, one or more of the channels can extend in a radial direction from an inner lumen or other interior portion of the tip electrode.

The illustrated embodiment in FIG. 7 shows a first spot electrode 521 adjacent an outer surface of the tip electrode 501. The first spot electrode 521 can comprise a thermal sensor. The first spot electrode 521 can be secured within the first channel 515 with the first spot non-conductive portion 527. The first spot non-conductive portion 527 can be used to secure the first spot electrode 521 in a desired position in relation to the rest of the electrodes on the tip electrode 501. Similarly, the third spot non-conductive portion 529 can be used to secure the third spot electrode 523 in a desired position in relation to the rest of the electrodes on the tip electrode 501. The base portion 507 can also comprise at least one tip anchor 543. The at least one tip anchor 543 can be used to further secure the tip assembly 500 to a catheter shaft. The conductor assembly 503 can comprise a first conductor pair 545, a second conductor pair 547, and a third conductor pair 549. Each conductor pair can be electrically coupled to a spot electrode. In the illustrated embodiment, the first conductor pair 545 can be electrically coupled to the first spot electrode 521, the second conductor pair 547 can be electrically coupled to the second spot electrode (not shown), and the third conductor pair 549 can be electrically coupled to the third spot electrode 523. Each conductor pair can enter the tip electrode 501 through the inner lumen 533 and then travel through one of the channels in the tip electrode 501. In one embodiment, the tip assembly can comprise a plurality of conductor pairs, with an individual conductor pair for each electrode on the tip electrode. It will be appreciated that the vias or channels may be completely metallized (as by interior wall coating or complete filling) in their interiors thus serving as conductive vias without discrete wires being placed therein. Alternatively they may be metallized therein only at the outer tip surface region during the deposition of the tip electrode conductive layer. Such partial channel or via metallization at the outer entry channel region allows for a wire to be soldered inside the channel near the tip surface-said wire being thus also connected to the adjacent surface electrode via the electrode layer metallization which also coats the tip surface in the form of defined electrodes.

Figure 8:
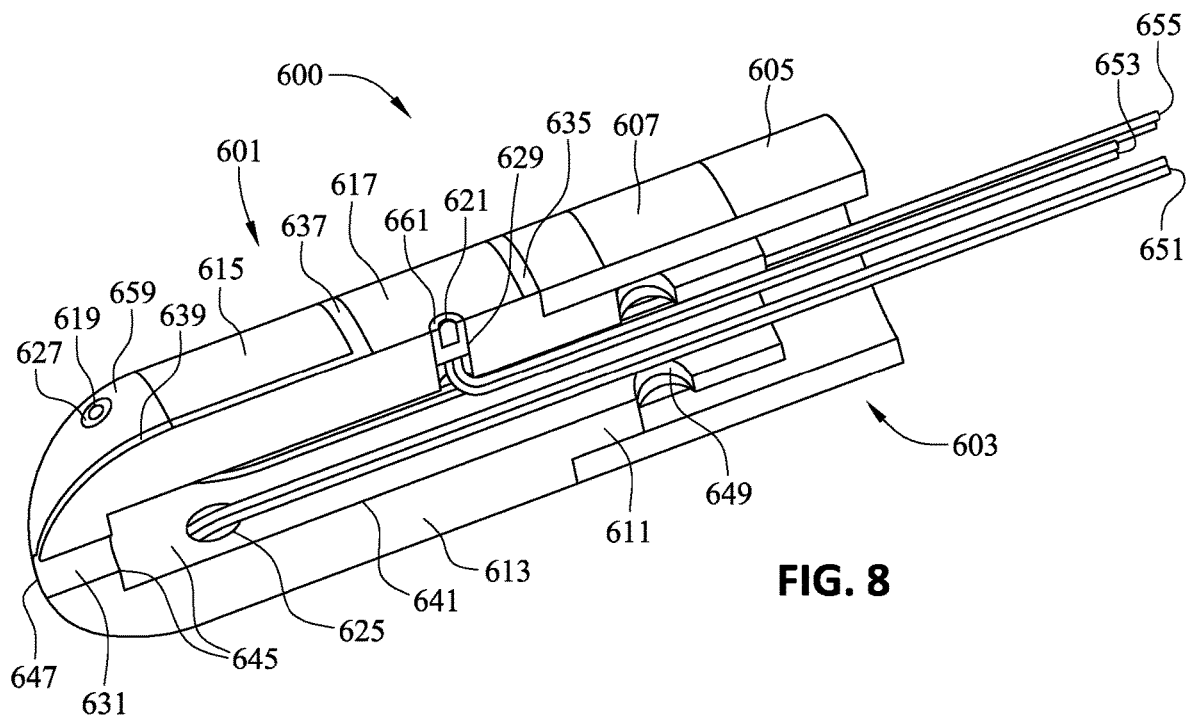
FIG. 8 is an isometric, cross-sectional view of another embodiment of a catheter assembly comprising a plurality of segmented tip electrodes and a plurality of spot electrodes.

FIG. 8 illustrates an isometric cross-sectional view of another embodiment of a catheter assembly 600. The catheter assembly can comprise a tip electrode 601 and a flexible catheter lumen body 603. The catheter body 603 can comprise a catheter shaft 605 and a ring electrode 607. The ring electrode 607 can be coupled to a distal portion of the catheter shaft 605. The tip electrode 601 can comprise a base portion 611 and can also comprise an electrically-insulative substrate 613. The tip electrode 601 can further comprise at least one segmented electrode 615, a tip ring electrode 617, a first spot electrode (not shown), a second spot electrode 619, a ring spot electrode 621, a first channel 625, a second channel 627, a third channel 629, a fourth channel 631, a proximal circumferential non-conductive portion 635, a distal circumferential non-conductive portion 637, a longitudinal non-conductive portion 639, and an inner tip surface 641. While not shown, other electrodes can be present on the tip electrode 601 as described throughout the disclosure. The inner tip surface 641 can define an inner lumen 645 that extends from a proximal end of the tip electrode 601 to a more distal portion of the tip electrode 601. The inner lumen 645 can be configured to allow for wires, irrigation lumens, or other desired components to be placed or routed through an inner portion of the tip electrode 601. The first channel 625, the second channel 627, the third channel 629, and the fourth channel 631 can extend from the inner tip surface 641 to an exterior tip surface. In the illustrated embodiment, each of the channels extends from an inner channel opening 645 to an outer surface opening 647. As seen in the illustrated embodiment, the channels (electrical vias, water ports or both) can be formed in various, different directions. The first channel 625 and the second channel 627 can extend in a distal direction from the inner tip surface 641 to the exterior tip surface. The third channel 629 can extend in a roughly 90 degree angle from the inner tip surface 641. The fourth channel 631 can extend from a distal end of the inner lumen 645 to a distal end of the tip electrode. In one embodiment, the fourth channel 631 can be sized and configured to couple to an irrigation lumen. In another embodiment, the fourth channel can be configured to fluidly couple to an irrigation source and can deliver an irrigant or other fluid to an exterior portion of the electrode tip. The base portion 611 of the electrode tip 601 can be configured to fit within the distal end of the catheter shaft 605. The base portion 611 can also comprise at least one tip anchor 649. In one embodiment, an adhesive can be used to couple the base portion 611 and the catheter shaft 605. In another embodiment, an adhesive can be used along with at least one anchor coupled to the at least one tip anchor 649. The catheter assembly 600 can further comprise a first conductor pair 651, a second conductor pair 653, and a third conductor pair 655. Each conductor pair can be electrically coupled to a thermocouple or spot electrode. For a spot electrode only one of the conductors can be used. For a thermocouple (or ablating electrode) both conductors can be used. For both a spot electrode and thermocouple in the same channel two conductors serve the thermocouple and at least one (or both) conductors serves the spot electrode. The necessary switching between the thermocouple function and electrode function can happen in the supporting system—conductor wires or metalized traces can be shared among functions. In the illustrated embodiment, the first conductor pair 651 can be electrically coupled to the first spot electrode (not shown), the second conductor pair 653 can be electrically coupled to the second spot electrode 619, and the third conductor pair 655 can be electrically coupled to the ring spot electrode 621. Each conductor pair can enter the tip electrode 601 through the inner lumen 645 and then travel through one of the channels in the tip electrode 601. In one embodiment, the tip assembly can comprise a plurality of conductor pairs, with an individual conductor pair for each electrode on the tip electrode. The second spot electrode 619 can be secured within the second channel 627 with a second spot non-conductive portion 659. The second spot non-conductive portion 659 can be used to secure the second spot electrode 619 in a desired position in relation to the rest of the electrodes on the tip electrode 601. Similarly, the ring spot electrode 621 can be secured within the third channel 629 with a ring spot non-conductive portion 661. The ring spot non-conductive portion 661 can be used to secure the ring spot electrode 621 in a desired position in relation to the rest of the electrodes on the tip electrode 601.

Figure 9:
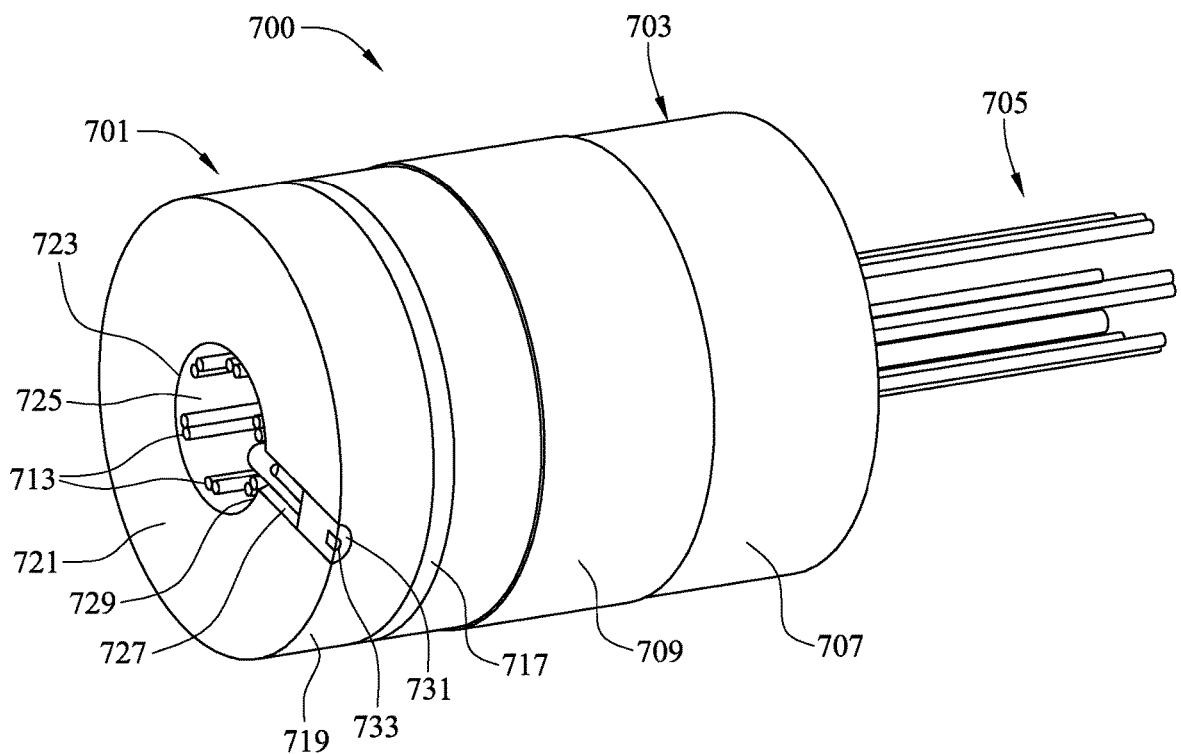
FIG. 9 is an isometric, cross-sectional view of another embodiment of a catheter assembly.

FIG. 9 illustrates an isometric, cutaway view of an embodiment of a catheter assembly 700. The catheter assembly can comprise a tip electrode 701, a conductor assembly 705, and a catheter body 703. The catheter body 703 can comprise a catheter shaft 707 and one or more ring electrodes 709 (one shown). The ring electrode(s) 709 can be coupled to a distal portion of the catheter shaft 707. The conductor assembly 705 can comprise a plurality of conductor pairs 713 or individual conductors. As stated above, a thermocouple or thermistor can use a pair of such conductors (e.g. copper and constantin conductors) whereas a spot electrode or RF ablation electrode needs at least one wire—preferably a copper or other high conductivity metal conductor. The tip electrode 701 can be coupled to the catheter body 703. The tip electrode 701 can comprise a proximal circumferential non-conductive portion 717, a tip ring electrode 719, an electrically-insulative substrate 721, an inner tip surface 723, an inner lumen 725, and a first channel 727. While not shown, other electrodes can be present on the tip electrode 701 as described throughout the disclosure. The inner tip surface 723 can define the inner lumen 725 that extends from a proximal end of the tip electrode to a more distal portion of the tip electrode. The channel 727 can extend from an inner channel opening 729 to an outer surface opening 731 and can extend from the inner tip surface 723 at a roughly 90 degree angle. A ring thermal sensor 733 can be secured within the third channel 727 with a ring sensor non-conductive portion 735. Each channel 72 can optionally support both an irrigation function and a thermocouple or electrode function.

Figure 10:
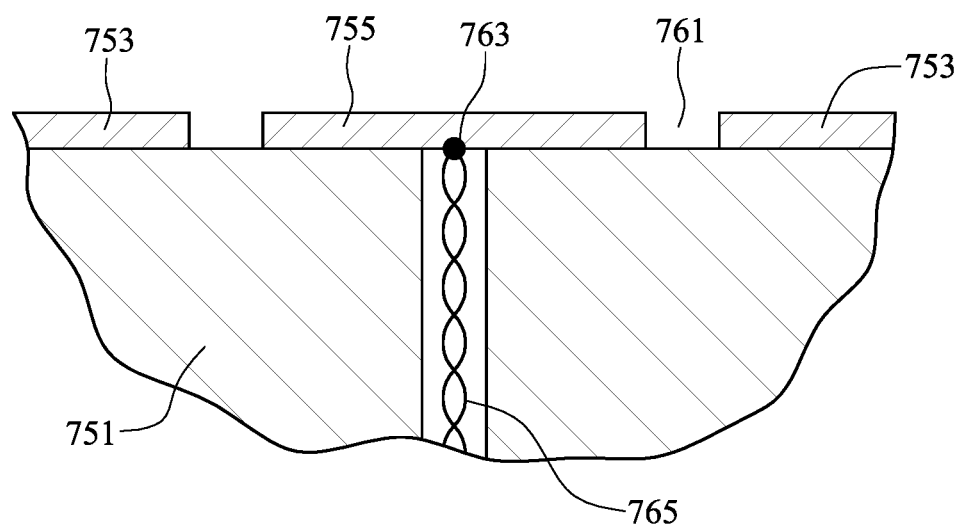
FIG. 10 is a close-up cross-sectional view of an embodiment of a tip electrode.

FIG. 10 illustrates a diagrammatic cross-sectional view of another embodiment of a tip electrode 750. The tip electrode 750 can comprise an electrically-insulative substrate 751, an ablation electrode 753, a spot electrode 755 situated within the ablation electrode 753 yet isolated from it by an insulative circular gap 761, a thermal sensor 763, and a conductor pair 765. The thermal sensor 763 is coupled to the conductor pair 765 and both can be electrically and thermally coupled to the spot electrode 755. The conductor pair 765 can transfer signals from the spot electrode 755 (via the copper wire) and the thermal sensor 763 (via both the copper and constantin wires) to a proximal end of a device as described above. The conductor pair 765 can also transfer energy to the thermal sensor 763 or spot electrode 755 if it is also employed to ablate as well as sense. The spot electrode 755 can be separated from the electrode 753 by the electrically insulative gap 761.

Figure 11:
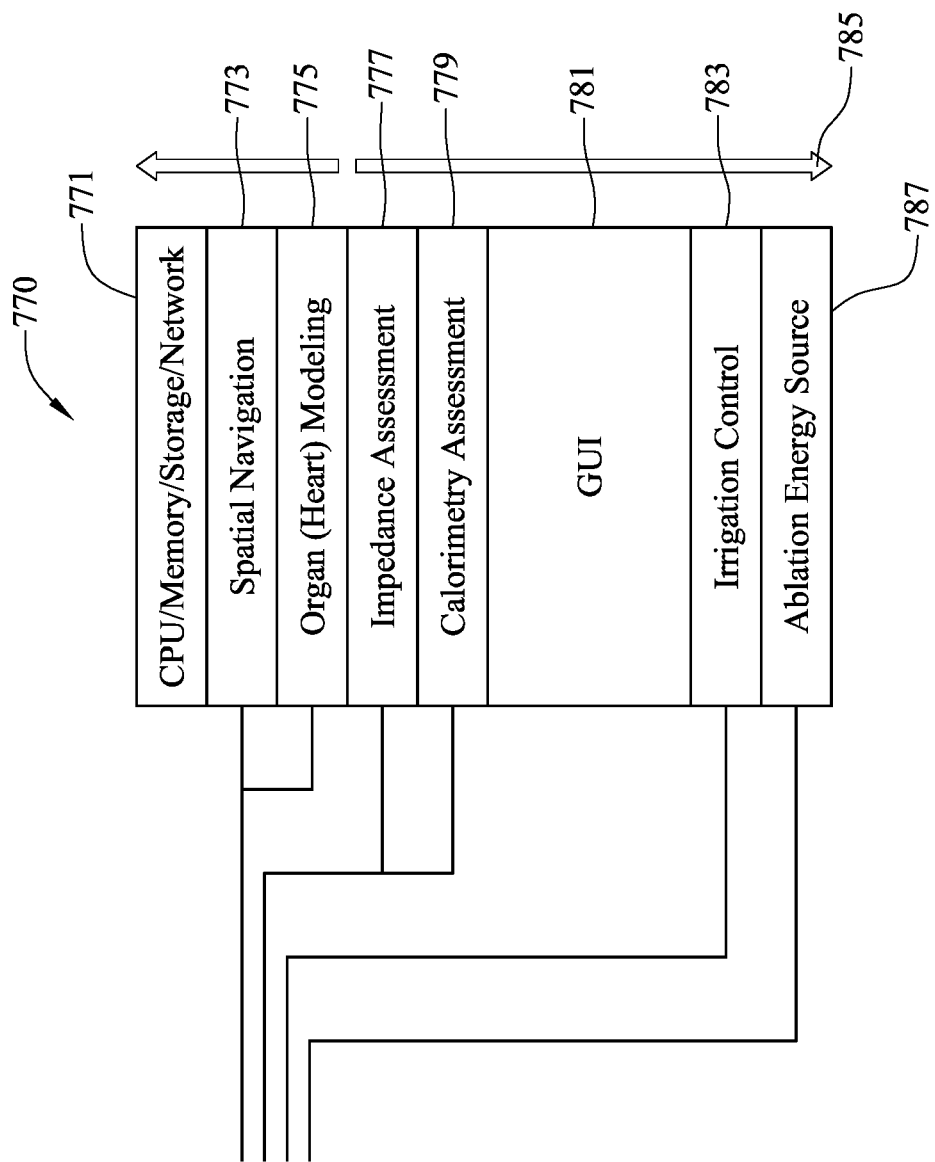
FIG. 11 is a diagrammatic view of a system that can be used for combining the independent impedance and calorimetry feedback from the electrodes on a catheter.

FIG. 11 is a diagrammatic view of a system 770 that can be used for combining the independent impedance and calorimetry lesion feedback from the electrodes on a catheter to deduce a lesion state and/or a temperature depth-profile if both feedback methods described above are employed. The lesion state can comprise a volume of the lesion, a depth of the lesion, a surface area of the lesion, a circumference of the lesion, or other states known to one of ordinary skill in the art. A weighting and/or combining algorithm can be used to make these determinations. Separate algorithms can be employed for the impedance and calorimetry methods themselves. Weighting can also be simple averaging (equal weight).

Again for intra-lesion bipolar electrical impedance feedback one connects across any two electrodes which both face the lesion. These may be two spot electrodes or a spot electrode and a larger ablating electrode surrounding it for example.

For pace and ablate feedback the split tip implementations of FIGS. 4, 5, and 6 can be bipolar paced in a novel manner that can utilize an even number of distal pacing electrodes. A pair of stimulator channels can be set for simultaneous pacing at the same duration and current strength such that pacing anodes and cathodes alternate. When adjusted to the pacing threshold, only the pair of electrodes in contact with cardiac tissue can be responsible for achieving capture. The pacing pulse strength may be set to an appropriate margin over the pacing threshold and thus catheter orientation independent pacing information quickly obtained. Pacing immediately prior to, during, and after RF application provides feedback on lesion effectiveness in a manner that complements electrogram signal reduction, tissue impedance changes, and calorimetry. Pace and ablate strategies can be valuable aids in the identification of lesion gaps. The pace and ablate procedure can be further seen in Eitel, C., Hindricks, G., Sommer, P. et al., Circumferential pulmonary vein isolation and linear left atrial ablation as single catheter technique to achieve bidirectional conduction block: the "pace-and-ablate" approach. Heart Rhythm. 2010; 7: 157-164, which is hereby incorporated by reference in its entirety as though fully set forth herein. In one embodiment, an electronic control unit can be configured to pace cardiac tissue by utilizing the segmented electrodes and spot electrodes disclosed herein.

Again, for calorimetry, we have thermocouples which face tissue and themselves sit on a thermally insulating tip material such as ceramic or polymer. We also have an adjacent or surrounding ablation electrode facing (and causing) the lesion. Using known RF thermal modeling techniques (earlier reference) we can make a depth-wise thermal profile model which incorporates decreasing thermal conductivity (and specific heat) of the tissue with extent of necrosis or lesioning. In this manner a bolus of injected heat (as by an RF power pulse), when stopped, will result in a thermal temperature decay at the tissue surface detectable by the surface contacting thermocouple(s). This decay curve is fitted to an assumed temperature and thermal conductivity profile that caused it. The initial starting assumption (before any lesion formation) is a decreasing temperature with depth and no thermal conductivity change (initially no necrosis has occurred). As the lesion progresses decreased thermal conductivity and specific heat is assumed (as caused by lesioning necrosis progressing downwards) such that the surface temperature decay curve is matched by the models current temperature and conductivity profile. Increasing degrees of tissue thermal exposure can result in increasing loss of thermal conductivity and specific heat as dewatering occurs. Full necrosis is the final state. Thus the changes are gradual which can allow for a feedback loop to automatically control ablation.

In another embodiment, the use of combined electrical impedance and calorimetry lesion-feedback tools can be configured to be acquired by impedance and calorimetry sensors that can be built upon an electrically and thermally insulating substrate. These two insulating qualities (electrical and thermal) can assure that the two feedback methods are sampling only the adjacent facing and underlying forming lesion. A number of possible calorimetric algorithms can be employed whether based on the incorporated references cited above, or using a new algorithm. This disclosure is not limited to a particular algorithm. Further, the two outputs, the electrical impedance, and the calorimetric information can have their corresponding presumed lesion depths be weighted in any desired manner such as 50/50 or equally wherein they are averaged.

It can be further noted that navigation magnetic coils (not shown) can easily be embedded or contained within the ceramic tip and that the navigation magnetic coil connecting wires can also perform shared duty as optionally might the thermal sensors.

In some embodiments, the system can comprise an ECU. FIG. 11 depicts a very generalized schematic of an overall system for performing EP procedures while taking benefit of the disclosure herein. The tip electrodes depicted above can be mounted on a catheter shaft which can in turn be connected to a catheter control handle. A variety of power, data and fluid lines can connect the catheter to the system 770. In the illustrated embodiment, the system 770 can comprise a computing module 771 (such as for impedance modeling, calorimetric modeling, heart chamber mapping and modeling), a spatial navigation module 773, an organ modeling module 775, an impedance assessment module 777, a calorimetry assessment module 779, a GUI module 781, an irrigation control module 783, an ablation module 787, and a communication module 785. In some embodiments the modules of the system 770 can be packaged together or share the same circuitry or software. In other embodiments, the modules of the system 770 can be separate. The computing module 771 can comprise the computational and logic means supporting the system 770 and can allow the system 770 to communicate to the outside world. Such computations and logic can be performed in software, firmware, or hardware. The spatial navigation module 773 can comprise the circuitry needed to create and sense navigation electric fields and/or magnetic fields. The spatial navigation module 773 can also comprise known magnetic or electromagnetic coils or body patches outside the spatial navigation module itself. The organ modeling module 775 can comprise software which can be employed to create a 3D/4D heart model. It may take navigation data, such as position and orientation, from the spatial navigation module 773 to do so. The impedance assessment module 777 can comprise circuitry and sensing such that the electrical impedance between desired pairs of catheter tip electrodes or sub-electrodes can be measured from within the single multi-electrode tip from electrodes touching the lesion and being at a known real time temperature. The calorimetry module 779 can comprise circuitry and sensing components such that select electrodes or sub-electrodes can be heated and or cooled (or irrigant flow can be step-changed) and resulting changing surface temperature detected in a manner that subsurface tissue heat flow can be deduced from at least one such reading and preferably from dual readings from tissue-facing adjacent electrodes. Dual adjacent readings can allow the module to better determine the rotational alignment of the tip to the lesion and a more accurate heat flow model can be made. In one embodiment, the employed electrodes face the tissue and their real time temperatures are known. The GUI module 781 can comprise circuitry to allow a user to communicate with and control the system 770. In this manner the GUI module 781 can provide system controls, system outputs, heart models showing the overlaid catheter and lesioning-extent, EP waveforms, patient info, lesion maps, EP Mapping data, etc. The irrigation control module 783 can comprise circuitry comprising a pump, logic for turning an irrigation or saline pump on/off or for varying its flow rate in support of ablation and feedback methods. In one embodiment, the irrigation control module can further comprise an irrigation or saline pump. The ablation module 787 can comprise an existing standalone RF generator as well as a supporting irrigation pump. In other embodiments, the ablation module can comprise a modularized co-packaged RF generator. In yet other embodiments, other ablative energy sources are included in the scope such as laser, microwave, ultrasonic ablation, electroporation and cryo. The communication module 785 can comprise a data/signal/power bus that can allow the various modules to be powered, share the CPU, share navigation feedback, share temperature feedback, share power supplies, and share sensing circuitry. In some embodiments, the power supplies and sensing circuitry can be shared between only portions of the system and in other embodiments the power supplies and sensing circuitry can be shared between the entire system. In yet other embodiments, the power supplies and the sensing circuitry can be shared between none of the modules in the system.

Figure 12A:
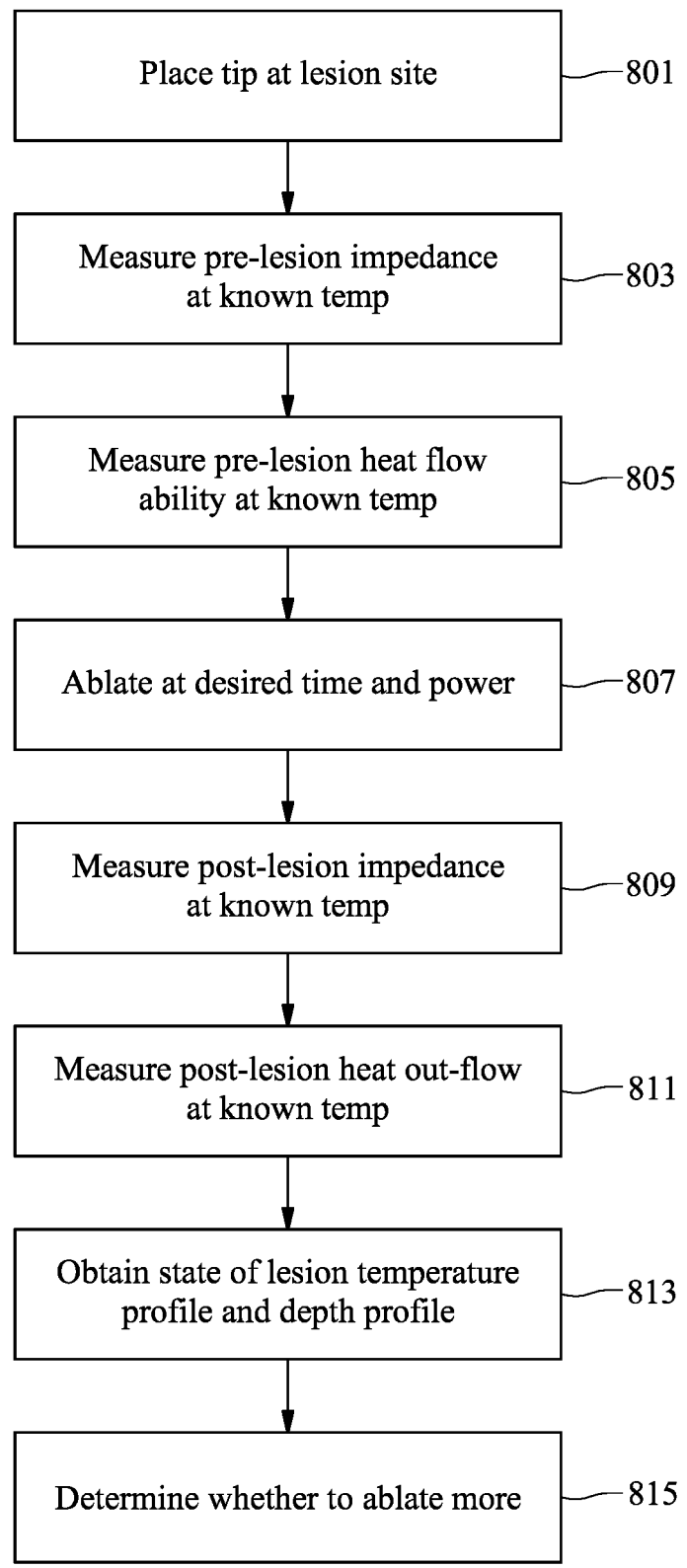
FIGS. 12A-12D are flowcharts for a method to utilize impedance feedback and/or heat flow feedback methods to determine a lesion state.

FIG. 12A depicts a flowchart for applying a method to utilize both impedance feedback and heat flow (calorimetry) feedback methods to determine a lesion state as described above. Step 801 comprises placing a catheter tip at a target tissue location at a desired lesion site. Step 803 comprises measuring a pre-lesion impedance of the target tissue location at a known cardiac starting temperature of about 37 deg C. Step 805 comprises measuring a pre-lesion heat-flow ability of the target tissue location at a known starting and peak temperatures wherein the peak temperature is below lesioning temperature, for example 40 or 41 deg C. Step 807 comprises incrementally ablating the target tissue location for a desired incremental time and at a desired power. Step 809 comprises measuring a post-lesion (post lesion increment) impedance of the target tissue location at a known starting achieved peak temperature. Step 811 comprises measuring a post-lesion heat-flow ability of the target tissue location at a known starting achieved peak surface temperature. Step 813 comprises obtaining a state of the lesion temperature profile and depth profile. The state of the lesion temperature profile and the depth profile can be determined by using the impedance and the heat flow values (scalar quantities) in to a tissue model. The states can be determined at the moment when power was temporarily discontinued. Step 815 comprises determining whether to further ablate the target tissue location. In one embodiment of step 815 the impedance feedback and the calorimetric feedback can be combined to determine whether further ablation of the target tissue location is desired.

Figure 12B:
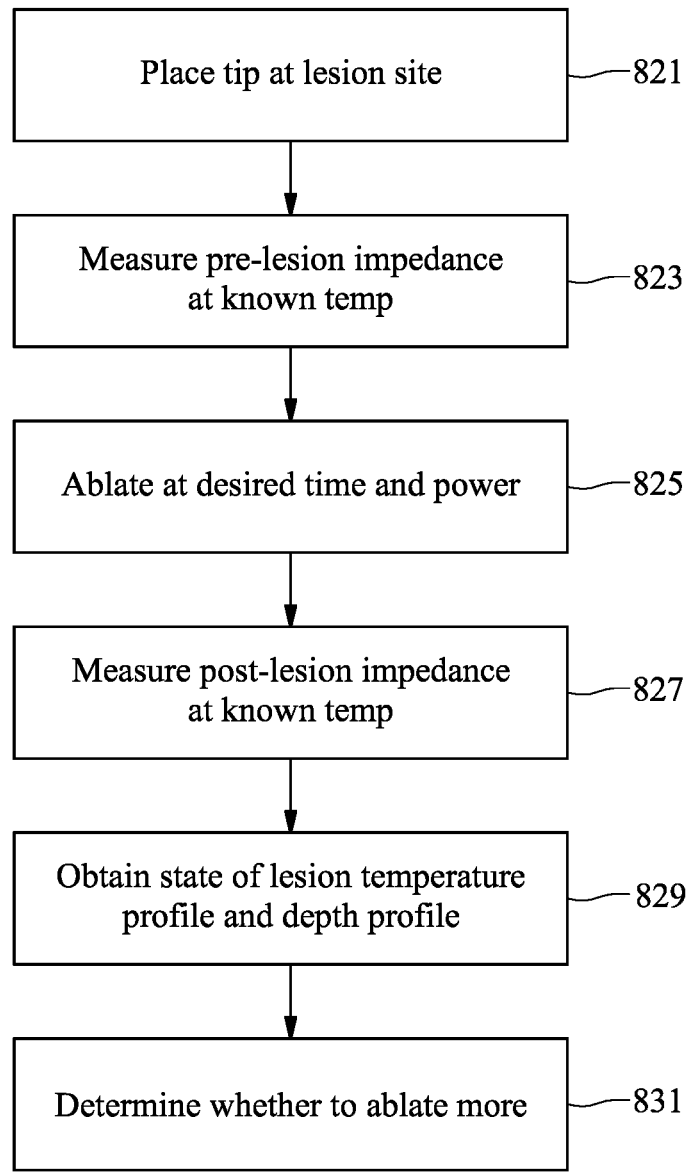

FIG. 12B depicts a flowchart for applying a method to utilize an impedance feedback method to determine a lesion state as described above. Step 821 comprises placing a catheter tip at a target tissue location at a desired lesion site. Step 823 comprises measuring a pre-lesion impedance of the target tissue location at a known temperature. Step 825 comprises incrementally ablating the target tissue location for a desired time and at a desired power. Step 827 comprises measuring a post-lesion impedance of the target tissue location at a known temperature such as at the achieved peak temperature. Step 829 comprises obtaining a state of the lesion temperature profile and depth profile. The state of the lesion temperature profile and the depth profile can be determined by using the impedance and the heat flow values (scalar quantities) in to a tissue model. The states can be determined at the moment when power was temporarily discontinued. Step 831 comprises determining whether to further ablate the target tissue location.

Figure 12C:
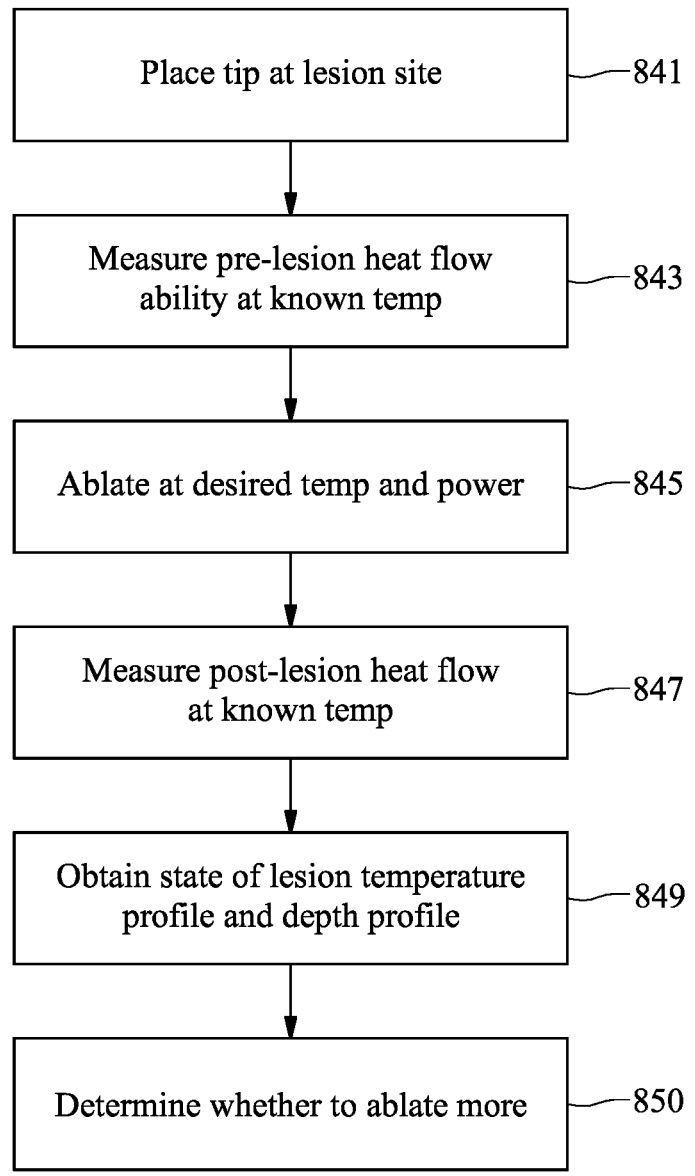

FIG. 12C depicts a flowchart for applying a method to utilize a heat flow feedback method to determine a lesion state as described above. Step 841 comprises placing a catheter tip at a target tissue location at a desired lesion site. Step 843 comprises measuring a pre-lesion heat-flow ability of the target tissue location at a known temperature. Step 845 comprises incrementally ablating the target tissue location for a desired time and at a desired power. Step 847 comprises measuring a post-lesion heat-flow ability of the target tissue location at a known achieved peak starting temperature. Step 849 comprises obtaining a state of the lesion temperature profile and depth profile. The state of the lesion temperature profile and the depth profile can be determined by using the impedance and the heat flow values (scalar quantities) in to a tissue model. The states can be determined at the moment when power was temporarily discontinued. Step 850 comprises determining whether to further ablate the target tissue location.

Figure 12D:
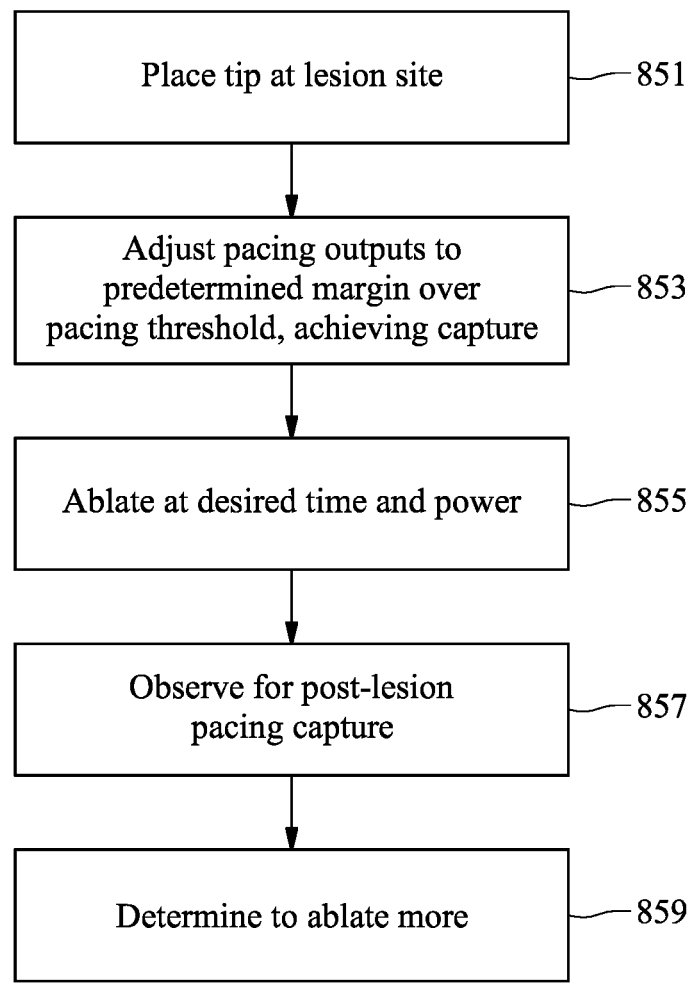

FIG. 12D depicts a flowchart for applying a method to utilize a pacing capture feedback method to determine a lesion state as described above. Step 851 comprises placing a catheter tip at a target tissue location at a desired lesion site. Step 853 comprises adjusting pacing outputs to a predetermined margin over the pacing threshold which just maintains capture. Step 855 comprises incrementally ablating the target tissue location for a desired time and at a desired power. Step 857 comprises observing for post lesion pacing capture. Step 859 comprises determining whether to further ablate the target tissue location.

In other embodiments, any of the methods listed in FIGS. 12A-12D can be used, but ablation at the target tissue can be stopped at least once during ablation to assess lesioning progress. In other embodiments, any of the methods listed in FIGS. 12A-12D can be used, and OIS assessments of electrogram signals as discussed above can also be performed while the method is being performed. In other embodiments, where the spot electrodes as discussed above are present on the catheter, the spot electrodes can monitor impedance throughout the ablation or at certain sampling times before, during, or after ablation. This can occur separate from the electrodes that are ablating the target tissue. In one embodiment, calorimetry can also be performed. In other embodiments, irrigation can be provided adjacent the catheter tip. In one embodiment, the irrigant is flow-excluded from the tissue-facing tip surface, but can still maintain a desired max temperature around the tip. In another embodiment, the irrigant flow can be provided at a temperature or flow rate which can deliver a desired cooling, warming, or temperature stabilizing effect on at least a portion of the tip. This effect can be caused for purposes of controllably practicing one or both lesion feedback methods. In on embodiment, the catheter can comprise 5 or 6 major electrodes running from the distal tip partway up the tip. This multi-electrode distal tip region can be guaranteed to contain a good tissue, high-percentage contact region-particularly if a minimum tip force is maintained. In this embodiment, the major electrodes are not present all the way up the tip such that that none of the feedback electrodes have significant blood flow around them such as at the proximal tip region which may sit off the tissue surface. In some embodiments, that flow can significantly affect both feedback methods.

What is claimed is:

1. A tip electrode comprising:
   an electrically insulative substrate comprising an inner lumen, an external tip surface, and a plurality of channels extending from the inner lumen to the external tip surface, wherein the electrically insulative substrate comprises a rigid material;
   a plurality of segmented electrodes,
   a plurality of wire or conductor traces and
   a plurality of spot electrodes;
   wherein at least one of the plurality of segmented electrodes is disposed on the electrically insulative substrate, wherein each of the plurality of segmented electrodes and each of the plurality of spot electrodes are laterally separated from each other by an electrically insulative gap and wherein each of the spot electrodes and each of the segmented electrodes are electrically coupled to at least one of the plurality of wire or conductor traces.

2. The tip electrode according to claim 1 further comprising a plurality of thermal sensors, wherein at least one of the plurality of thermal sensors is disposed within a channel and is adjacent the external tip surface.

3. The tip electrode according to claim 2, wherein at least one of the plurality of thermal sensors is disposed adjacent one of the plurality of spot electrodes such that the thermal sensor can be electrically connected to a conductor pair electrically connected to the spot electrode.

4. The tip electrode according to claim 1 further comprising an irrigation through hole extending through the electrically-insulative substrate.

5. The tip electrode according to claim 4, wherein said irrigation through hole comprises a channel which acts to deliver irrigant and in addition contains at least one electrode or thermal sensor wire or conductor.

6. The tip electrode according to claim 1, wherein at least one of the plurality of wire or conductor traces comprises a conductor pair and wherein a thermal sensor is electrically coupled to the conductor pair.

7. The tip electrode according to claim 1, wherein at least one of the plurality of spot electrodes is disposed within the lateral confines of an ablating electrode segment.

8. The tip electrode according to claim 1, wherein at least one of the plurality of channels comprises a metallized surface to electrically couple one of the plurality of spot electrodes or one of the plurality of segmented electrodes to the at least one wire or conductor trace.

9. The tip electrode according to claim 1, wherein the plurality of segmented electrodes comprises at least three segmented electrodes.

10. The tip electrode according to claim 9, wherein the plurality of spot electrodes comprises at least three spot electrodes.

11. The tip electrode according to claim 10 wherein each of the spot electrodes is disposed within a separate segmented electrode.

12. The tip electrode according to claim 11, wherein each of the spot electrodes is disposed within a distal portion of the electrically insulative substrate.

13. The tip electrode according to claim 1 further comprising a tip ring electrode.

14. The tip electrode according to claim 13 wherein the tip ring electrode is disposed proximal of the plurality of segmented electrodes.

15. The tip electrode according to claim 14 further comprising a ring spot electrode.

16. The tip electrode according to claim 15, wherein the ring spot electrode is surrounded by the tip ring electrode.

17. The tip electrode according to claim 1, wherein each of the plurality of segmented electrodes extend in a longitudinal direction along a length of the tip.

18. The tip electrode according to claim 17 further comprising a distal end non-conductive portion.

19. The tip electrode according to claim 17 further comprising an irrigation through-hole at a distal end of the electrically insulative substrate.

20. The tip electrode according to claim 17 further comprising a plurality of longitudinal non-conductive portions.

21. The tip electrode according to claim 20 wherein each of the plurality of segmented electrodes is bordered by two of the plurality of longitudinal non-conductive portions.

22. The tip electrode of claim 1 wherein the electrically insulative substrate comprises alumina, zirconia, zirconia-toughened alumina or silicon nitride.

23. The tip electrode according to claim 1, wherein at least one of the plurality of segmented electrodes disposed on the electrically insulative substrate comprises a vapor deposited metal on the ceramic material.

24. A system for ablating tissue comprising:
   a tip electrode comprising:
      an electrically insulative substrate comprising an inner lumen, an external tip surface, and a plurality of channels extending from the inner lumen to the external tip surface, wherein the electrically insulative substrate comprises a ceramic material;
      a plurality of segmented electrodes, and
      a plurality of spot electrodes;
      wherein at least one of the plurality of segmented electrodes is disposed on the electrically insulative substrate, wherein each of the plurality of segmented electrodes and each of the plurality of spot electrodes are laterally separated from each other by an electrically insulative gap and wherein each of the spot electrodes and each of the segmented electrodes are electrically coupled to at least one wire or conductor; and
   an electronic control unit configured to control the plurality of spot electrodes and the plurality of segmented electrodes to bipolar pace cardiac tissue.

25. A tip electrode comprising:
   an electrically insulative substrate comprising an inner lumen, an external tip surface, and a plurality of channels extending from the inner lumen to the external tip surface;
   a plurality of segmented electrodes,
   a plurality of wire or conductor traces and
   a plurality of spot electrodes;
   wherein at least one of the plurality of segmented electrodes is disposed on the electrically insulative substrate, wherein each of the plurality of segmented electrodes and each of the plurality of spot electrodes are laterally separated from each other by an electrically insulative gap, wherein at least one of the plurality of spot electrodes is disposed within the confines of an ablating electrode segment, wherein each of the spot electrodes and each of the segmented electrodes are electrically coupled to at least one of the plurality of wire or conductor traces, wherein at least one of the plurality of channels extends in a radial direction to at least one of the spot electrodes, wherein at least one of the plurality of spot electrodes is disposed within an ablating electrode segment.

* * * * *